US012752274B2

(12) United States Patent
Tse et al.

(10) Patent No.: US 12,752,274 B2
(45) Date of Patent: Oct. 6, 2026

(54) SYSTEM AND METHOD FOR DETERMINING AN IMMUNE ACTIVATION STATE

(71) Applicant: CytoVale Inc., San Francisco, CA (US)

(72) Inventors: Henry Tat Kwong Tse, San Francisco, CA (US); Ajay M. Shah, San Francisco, CA (US); Lionel Guillou, San Francisco, CA (US); Alexander Malkin, San Francisco, CA (US); Anne E. Jensen, San Francisco, CA (US); Nicholas Martinez, San Francisco, CA (US); Carissa Colegrove, San Francisco, CA (US); Laura Voyen, San Francisco, CA (US)

(73) Assignee: CytoVale Inc., San Francisco, CA (US)

( * ) Notice: Subject to any disclaimer, the term of this patent is extended or adjusted under 35 U.S.C. 154(b) by 1066 days.

(21) Appl. No.: 17/841,470

(22) Filed: Jun. 15, 2022

(65) Prior Publication Data

US 2023/0219087 A1 Jul. 13, 2023

Related U.S. Application Data

(62) Division of application No. 17/575,388, filed on Jan. 13, 2022, now Pat. No. 11,548,003.

(51) Int. Cl.
*B01L 3/00* (2006.01)
*G01N 1/34* (2006.01)
(Continued)

(52) U.S. Cl.
CPC ... *B01L 3/502761* (2013.01); *B01L 3/502715* (2013.01); *G01N 1/34* (2013.01); *G01N 1/4044* (2013.01); *G01N 1/4077* (2013.01); *G01N 15/1434* (2013.01); *G01N 33/5094* (2013.01); *G16B 40/20* (2019.02);
(Continued)

(58) Field of Classification Search
None
See application file for complete search history.

(56) References Cited

U.S. PATENT DOCUMENTS 4,654,312 A 3/1987 Chang et al.
4,902,613 A 2/1990 Chang et al.
(Continued)

FOREIGN PATENT DOCUMENTS

CN 204490895 U * 7/2015
CN 109596403 A * 4/2019 ........... G01N 1/4077
(Continued)

OTHER PUBLICATIONS

CN 109596403 A Yang et al, English Translation (Year: 2019).*
(Continued)

*Primary Examiner* — Brittany I Fisher
(74) *Attorney, Agent, or Firm* — Wilson Sonsini Goodrich & Rosati

(57) ABSTRACT

A system or method for detecting an immune system activation state in a patient can include a sample preparation system configured to isolate white blood cells from a sample of the patient, a cytometry module configured to determine biophysical properties of the white blood cells of the sample, and an analysis module configured to analyze the biophysical properties.

20 Claims, 9 Drawing Sheets

(51) Int. Cl.

| | |
|---|---|
| ***G01N 1/40*** | (2006.01) |
| ***G01N 15/01*** | (2024.01) |
| ***G01N 15/14*** | (2024.01) |
| ***G01N 15/1433*** | (2024.01) |
| ***G01N 15/1434*** | (2024.01) |
| ***G01N 33/50*** | (2006.01) |
| ***G16B 40/20*** | (2019.01) |
| ***G16H 50/20*** | (2018.01) |
| ***G16H 50/30*** | (2018.01) |
| *G01N 15/10* | (2006.01) |

(52) U.S. Cl.

CPC .................. *B01L 2200/0663* (2013.01); *B01L 2300/0654* (2013.01); *G01N 2001/4088* (2013.01); *G01N 2015/011* (2024.01); *G01N 2015/016* (2024.01); *G01N 2015/1006* (2013.01); *G01N 2800/26* (2013.01)

(56) References Cited

U.S. PATENT DOCUMENTS

| | | | |
|---|---|---|---|
| 5,155,044 A | 10/1992 | Ledis et al. | |
| 5,656,499 A * | 8/1997 | Chupp | G01N 35/1004 436/805 |
| 5,798,827 A | 8/1998 | Frank et al. | |
| 8,935,098 B2 | 1/2015 | Di Carlo et al. | |
| 9,151,705 B2 | 10/2015 | Di Carlo et al. | |
| 9,414,990 B2 | 8/2016 | Ivosevic et al. | |
| 9,464,977 B2 | 10/2016 | Di Carlo et al. | |
| 9,522,344 B2 | 12/2016 | Di Carlo et al. | |
| 9,638,620 B2 | 5/2017 | Di Carlo et al. | |
| 9,897,532 B2 | 2/2018 | Di Carlo et al. | |
| 10,107,735 B2 | 10/2018 | Di Carlo et al. | |
| 10,252,260 B2 | 4/2019 | Tse et al. | |
| 10,808,219 B2 | 10/2020 | Masaeli et al. | |
| 10,967,296 B2 | 4/2021 | Di Carlo et al. | |
| 10,969,327 B2 | 4/2021 | Di Carlo et al. | |
| 11,169,078 B2 | 11/2021 | Di Carlo et al. | |
| 11,521,706 B2 | 12/2022 | Xin et al. | |
| 11,548,003 B1 | 1/2023 | Tse et al. | |
| 11,986,824 B2 | 5/2024 | Tse et al. | |
| 2005/0070005 A1 | 3/2005 | Keller | |
| 2005/0221396 A1 | 10/2005 | Simon-Lopez | |
| 2006/0139638 A1 | 6/2006 | Muller et al. | |
| 2006/0210438 A1* | 9/2006 | Nagai | G01N 15/14 422/73 |
| 2008/0077072 A1 | 3/2008 | Keenan et al. | |
| 2009/0014360 A1 | 1/2009 | Toner et al. | |
| 2013/0177935 A1 | 7/2013 | Di et al. | |
| 2013/0224851 A1* | 8/2013 | Ljungmann | B04B 5/0421 435/308.1 |
| 2014/0087412 A1 | 3/2014 | Fouras et al. | |
| 2014/0113324 A1* | 4/2014 | Di Carlo | G01N 15/1459 435/29 |
| 2014/0227777 A1 | 8/2014 | Choi et al. | |
| 2014/0315287 A1 | 10/2014 | Di Carlo et al. | |
| 2015/0238963 A1 | 8/2015 | Han et al. | |
| 2015/0355073 A1 | 12/2015 | Di Carlo et al. | |
| 2016/0231224 A1 | 8/2016 | Di Carlo et al. | |
| 2017/0089822 A1 | 3/2017 | Di Carlo et al. | |
| 2017/0234788 A1 | 8/2017 | Di Carlo et al. | |
| 2017/0284924 A1 | 10/2017 | Tse et al. | |
| 2018/0128735 A1 | 5/2018 | Di Carlo et al. | |
| 2018/0267021 A1 | 9/2018 | Suresh et al. | |
| 2018/0305758 A1 | 10/2018 | Shi et al. | |
| 2019/0092757 A1 | 3/2019 | Ashford et al. | |
| 2019/0143326 A1 | 5/2019 | Irimia et al. | |
| 2021/0031198 A1* | 2/2021 | Tse Kwong | B01L 3/502761 |
| 2021/0110545 A1 | 4/2021 | Herold et al. | |
| 2021/0181086 A1 | 6/2021 | Chou et al. | |
| 2023/0241612 A1 | 8/2023 | Tse et al. | |

FOREIGN PATENT DOCUMENTS

| | | | |
|---|---|---|---|
| EP | 2619545 | B1 | 1/2019 |
| JP | 2001211896 | A | 8/2001 |
| JP | 2009511998 | A | 3/2009 |
| KR | 100889617 | B1 | 3/2009 |
| KR | 100889618 | B1 | 3/2009 |
| KR | 100965222 | B1 | 6/2010 |
| WO | 2004113908 | A1 | 12/2004 |
| WO | 2007047761 | A1 | 4/2007 |
| WO | 2009069418 | A1 | 6/2009 |
| WO | 2012040067 | A2 | 3/2012 |
| WO | 2014113110 | A2 | 7/2014 |
| WO | 2018213721 | A1 | 11/2018 |
| WO | 2020011487 | A1 | 1/2020 |
| WO | 2021022050 | A1 | 2/2021 |
| WO | WO-2023136896 | A1 | 7/2023 |

OTHER PUBLICATIONS

CN 204490895 U, Wang et al, English Translation (Year: 2015).*

Espacenet English Translation of CN204490895U (Year: 2015).*

Minamitani, Haruyuki , et al., "Deformability Cytometry: High-Throughput, Continuous Measurement of Cell Mechanical Properties in Extensional Flow", BMES/EMBS Conference, 1999, Proceedings of the First Joint Atlanta, GA, USA Oct. 13-16, 1999, Piscataway, NJ, USA, IEEE, US, vol. 1, Oct. 13, 1999 (Oct. 13, 1999, p. 72, XPO10357477, Dol: 10.1109/IEMBS. 1999.802107, ISBN: 978-0-7803-5674-0.

Issekutz, Andrew C., "Role of ICAM-1 and ICAM-2 and alternate CD11/CD18 ligands in neutrophil transendothelial migration", 1999, 65, 117-126 (Year 199).

"BD FACS Lyse Wash Assistant Streamline Sample Preparation Workflow", BD Biosciences, For In Vitro Diagnostics Use, downloaded from the internet Dec. 13, 2021.

"BD FACS™ Lyse Wash Assistant", BD Biosciences, https://www.bdbiosciences.com/en-us/products/instruments/sample-prep-systems/facs-lyse-wash-assistant, downloaded from the internet Dec. 13, 2021.

"Cytovale", https://cytovale.com, downloaded from the internet Dec. 13, 2021.

"Phantom v7.3, Phantom Camera Products", http://www.visionresearch.com/Products/, downloaded Feb. 16, 2022.

"TQ-Prep Workstation", Beckman Coulter Lifesciences, https://www.beckman.com/flow-cytometry/instruments/tq-prep, downloaded from the internet Dec. 13, 2021.

Bhagat, Ali Asgar, et al., "Intertial microfluidics for sheath-less high-throughput cytometry", Biomed. Microdevices 12(2), 187-195 (2010)., Oct. 31, 2017 00:00:00.0.

Bow, Hansen , et al., "A microfabricated deformability-based flow cylometer with application to malaria", Lab Chip. Mar. 21, 2011; 11(6): 1065-1073. doi:10.1039/c0lc00472c.

Cha, Sukgyen , et al., "Cell Stretching Measurement Utilizing Viscoelastic Particle Focusing", Anal. Chem., 2012, 84, 10471-10477., Oct. 31, 2017 00:00:00.0.

Chambers, Ann F. , et al., "Metastasis: dissemination and growth of cancer cells in metastatic site", Nature Reviews cancer, vol. 2(8), p. 563-572, 2002.

Chen, J. , et al., "Classification of cell types using a microfluidic device for mechanical and electrical measurement on single cells", Lab Chip, 2011, 11, 3174-3181., Oct. 31, 2017 00:00:00.0.

Choi, Sungyoung , et al., "Sheathless hydrophoretic particle focusing in a microchannel with exponentially Increasing obstacle arrays", Anal Chem., 80(8):3035-9 (2008)., Oct. 31, 2017 00:00:00.0.

Crawford, Katherine , et al., "Rapid Biophysical Analysis of Host Immune Cell Variations Associated with Sepsis", American Journal of Respiratory and Critical Care Medicine, vol. 198, No. 2, Jul. 15, 2018.

Cross, Sarah E., et al., "Nanomechanical analysis of cells from cancer patients", Nat Nano 2:780-783 (2007)., Oct. 31, 2017 00:00:00.0.

(56) References Cited

OTHER PUBLICATIONS

Di Carlo, Dino , et al., "Continuous inertial focusing, ordering, and separation of particles in microchannels", Proc Natl Acad Sci USA 104:18892-18897 (2007)., Oct. 31, 2017 00:00:00.0.
Di Carlo, Dino , et al., "Dynamic Single-Cell Analysis for Quantitative Biology", Analytical Chemistry 78:7918-7925 (2006)., Oct. 31, 2017 00:00:00.0.
Di Carlo, Dino , et al., "Inertial microfluidics", Lab Chip 9:3038-3046 (2009)., Oct. 31, 2017 00:00:00.0.
Di Carlo, Dino , et al., "Particle Segregation and Dynamics in Confined Flows", Phys. Rev. Lett. 102 (2009)., Oct. 31, 2017 00:00:00.0.
Dobbe, J.G.G. , et al., "Measurement of the Distribution of Red Blood Cell Deformability Using an Automated Rheoscope", Cytometry (Clinical Cytometry), vol. 50, pp. 313-325, 2002.
Dudani, Jaideep S., et al., "Pinched-flow hydrodynamic stretching of single-cells", Lab Chip, 2013, 13, 3728., Oct. 31, 2017 00:00:00.0.
Dylla-Spears, Rebecca , et al., "Single-molecule detection via microfluidic planar extensional flow at a stagnation point", Lab on a Chip, vol. 10, pp. 1543-1549, Mar. 2010., Oct. 31, 2017 00:00:00.0.
Fardi, Muhammad Asim , et al., "Elasto-inertial microfluidics for bacteria separation from whole bloods for sepsis diagnostics", Journal of Nanobiotechnology, (2017) 15:3.
Fregin, Bob , et al., "High-throughput single-cell rheology in complex samples by dynamic real-time deformability cytometry", Nature Communications, (2019)10:415.
Gossett, D.R. , et al., "Deformability Cytometry: High-Throughput, Continuous Measurement of Cell Mechanical Properties in Extensional Flow", 14th International Conference on Miniaturized Systems for Chemistry and Life Sciences Oct. 3-7, 2010, Groningen, The Netherlands.
Gossett, Daniel R., et al., "Hydrodynamic stretching of single cells for large population mechanical phenotyping", 7630-7635, PNAS, May 15, 2012, vol. 1091, No. 20., Oct. 31, 2017 00:00:00.0.
Gossett, Daniel R., et al., "Label-free cell separation and sorting in microfluidic systems", Apr. 25, 2010, Springer, Anal. Bioanal. Chem., 397, pp. 3249-3267.
Gossett, Daniel R., et al., "Leukocyte Mechanophenotyping by Deformability Cytometry", 16th International Conference on Miniaturized Systems for Chemistry and Life Sciences Oct. 28-Nov. 1, 2012, Okinawa, Japan (3 pages).
Gossett, Daniel R., et al., "Particle focusing mechanisms in curving confined flows", Anal Chem 81:8459-8465 (2009).
Guck, J. , et al., "Optical Deformability as an Inherent Cell Marker for Testing Malignant Transformation and Metastatic Competence", Biophysical Journal, vol. 88, May 2005, 3689-3698., Oct. 31, 2017 00:00:00.0.
Guillou, Lionel , et al., "Development and validation of a cellular host response test as an early diagnostic for sepsis", PLOS One, Research Article, Apr. 15, 2021.
Gunsolus, Ian L., et al., "Diagnosing and Managing Sepsis by Probing the Host Response to Infection: Advances, Opportunities, and Challenges", Journal of Clinical Microbiology, vol. 57, Issue 7, Jul. 2019.
Guo, Q. , "Microfluidic Device for Measuring the Deformability of Single Cells", Doctorate Thesis, The University of British Columbia, Apr. 2012, 1-24 (total 78 pages., Oct. 31, 2017 00:00:00.0.
Lee, Wonhee , et al., "Dynamic self-assembly and control of microfluidic particle crystals", Proc. Natl. Acad. Sci. U.S.A 107, 22413-22418 (2010)., Oct. 31, 2017 00:00:00.0.
Lincoln, Bryan , et al., "Deformability-Based Flow Cytometry", Cytometry Part A, vol. 59A, pp. 203-209, 2004.
Mao, Xiaole , et al., "Single-layer planar on-chip flow cytometer using microfluidic drifting based three-dimensional (3D) hydrodynamic focusing", Lab Chip, 9, 1583-1589 (2009)., Oct. 31, 2017 00:00:00.0.
Morton, K.J. , et al., "Crossing microfluidic streamlines to lyse, label and wash cells", Lab Chip 8, 1448-1453 (2008).
Mutlu, Baris R., et al., "Oscillatory inertial focusing in infinite microchannels", PNAS, vol. 115, No. 30, 7682-7687, Jul. 24, 2018.
Natu, Rucha , et al., "Assessment of Flow through Microchannels for Inertia-Based Sorting: Steps toward Microfluidic Medical Devices", Micromachines, 2020, 11, 886, published Sep. 24, 2020.
Oakey, John , et al., "Particle Focusing in Staged Inertial Microfluidic Devices for Flow Cytometry", Anal. Chem., 82, 3862-3867 (2010)., Oct. 31, 2017 00:00:00.0.
Oeschger, Taylor , et al., "Point of care technologies for sepsis diagnosis and treatment", Lab Chip, 2019, 19, 728-737.
Park, Jae-Sung , et al., "Continuous focusing of microparticles using intertial lift force and vorticity via multi-orifice microfluidic channels", Lab on a Chip, 9, 939-48 (2009)., Oct. 31, 2017 00:00:00.0.
Perkins, Thomas T., et al., "Single Polymer Dynamics in an Elongational Flow", Science 276:2016-2021 (1997)., Oct. 31, 2017 00:00:00.0.
Petersson, F. , et al., "Carrier Medium Exchange through Ultrasonic Particle Switching in Microfluidic Channels", Anal. Chem. 77, 1216-1221 (2005).
Sawetzki, Tobias , et al., "Viscoelasticity as a Biomarker for High-Throughput Flow Cytometry", Biophysical Journal, vol. 105, Nov. 2013, pp. 2281-2288.
Shelby, Patrick J., et al., "A microfluidic model for single-cell capillary obstruction by Plasmodium falciparum-infected erythrocytes", PNAS, vol. 100, pp. 14618-14622, 2003., Oct. 31, 2017 00:00:00.0.
Squires, Todd M., "Microfluidics: Fluid physics at the nanoliter scale", Rev. of Modern Physics, vol. 77, pp. 977-1026, 2005., Oct. 31, 2017 00:00:00.0.
Sraj, Ihab , et al., "Cell deformation cytometry using diode-bar optical stretchers", J Biomed Opt 15 (2010)., Oct. 31, 2017 00:00:00.0.
Suresh, S. , et al., "Connections between single-cell biomechanics and human disease states: gastrointestinal cancer and malaria", Acta Biomater 1:15-30 (2005)., Oct. 31, 2017 00:00:00.0.
Thery, Manuel , et al., "Get round and stiff for mitosis", HFSP J 2:65-71 (2008)., Oct. 31, 2017 00:00:00.0.
Tornay, R. , et al., "Dielectrophoresis-based particle exchanger for the manipulation and surface functionalization of particles", Lab Chip 8, 267-273 (2008).
Ellet Felix, "Diagnosis of sepsis from a drop of blood by measurement of spontaneous neutrophil motility in a microfluidic assay", Nature biomedical engineering 2.4 (2018): 207-214. (Year: 2018).
Tse, Henry T.K., et al., "Quantitative Diagnosis of Malignant Pleural Effusions by Single-Cell Mechanophenotyping", Science Translational Medicine, Nov. 20, 2013: vol. 5, Issue 212, pp. 212ra163.
Yamada, Masumi , et al., "Hydrodynamic filtration for on-chip particle concentration and classification utilizing microfluidics", Lab Chip, 5, 1233-1239 (2005).
Yamada, M. , et al., "Millisecond treatment of cells using microfluidic devices via two-step carrier medium exchange", Lab Chip, 8, 772-778 (2008).
Yap, Belinda , et al., "Cystoskeletal remodeling and cellular activation during deformation of neutrophils into narrow channels", J. Appl. Physiol, vol. 99, pp. 2323-2330, 2005., Oct. 31, 2017 00:00:00.0.
Young, Susan M., et al., "High-Throughput Microfluidic Mixing and Multiparametric Cell Sorting for Bioactive Compound Screening", J. Biomol Scree, vol. 9, pp. 103-111, 2004.
Zhang, Xunil , et al., "Continuous flow separation of particles within an asymmetric microfluidic device", 2006, RSC, cab Chip, 6, 561-566.
Zhang, J. , et al., "Inertial focusing in a straight channel with asymmetrical expansion-contraction cavity arrays using two secondary flows", J. Micromech. Microeng. 23 (2013) 08023 (13pp).
Zheng, Bo , et al., "Formation of Droplets of Alternating Composition in Microfluidic Channels and Applications to Indexing of Concentrations in Droplet-Based Assays", Anal. Chem., vol. 76, pp. 4977-4982, 2004., Oct. 31, 2017 00:00:00.0.
Jalali, Bahram , et al., "Evolution of Photonic Time Stretch: From Analog to Digital Conversion to Blood Screening", arXiv:1106.5518 physics.ins-det, Submitted Jun. 27, 2011.

(56) References Cited

OTHER PUBLICATIONS

Rosenbluth, Michael J, "Analyzing cell mechanics in hematologic diseases with microfluidic biophysical flow cytometry", Lab on a Chip 8.7 (2008): 1062-1070. (Year: 2008.
EP22920944.0 Extended European Search Report dated Nov. 28, 2025.
Laws et al.: Neutrophils are the predominant cell-type to associate within a BALB/c mouse model of respiratory melioidosis. Microbial Pathogenesis, Academic Press Limited. 51(6):471-475 (2011).
PCT/US2022/052236 International Preliminary Report on Patentability dated Jul. 25, 2024.
PCT/US2022/052236 International Search Report and Written Opinion dated May 23, 2023.
U.S. Appl. No. 17/575,388 Office Action dated Jul. 15, 2022.

* cited by examiner

SYSTEM AND METHOD FOR DETERMINING AN IMMUNE ACTIVATION STATE

CROSS-REFERENCE TO RELATED APPLICATIONS

This application is a divisional of U.S. patent application Ser. No. 17/575,388 filed 13 Jan. 2022, which is incorporated in its entirety by this reference.

TECHNICAL FIELD

This invention relates generally to the health field, and more specifically to a new and useful system and method in the health field.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1:
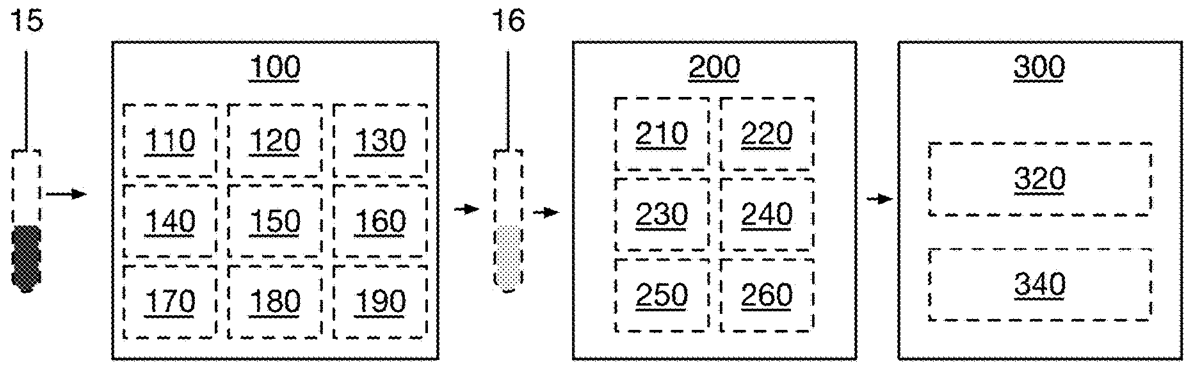
FIG. 1 is a schematic representation of an example of the apparatus.

As shown in FIG. 1, the system 10 can include a sample preparation module, a measurement module, a computing system, and/or any suitable components.

Figure 2:
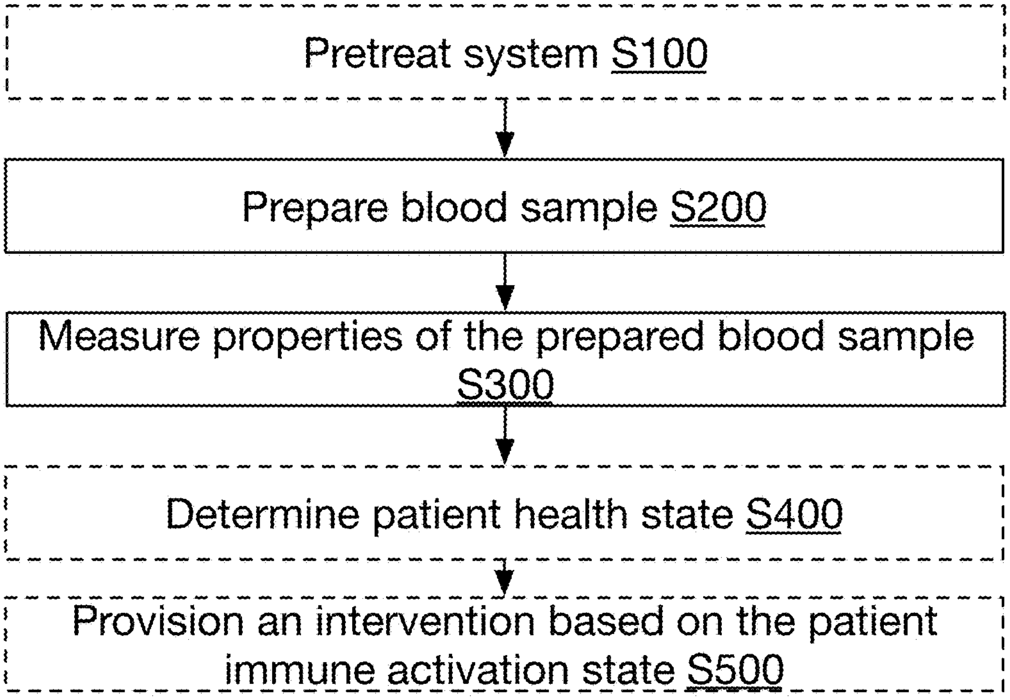
FIG. 2 is a schematic representation of an example of the method.

As shown in FIG. 2, the method 20 can include preparing a sample and measuring the sample. The method can optionally include: pretreating the system (or portions thereof), determining an immune activation state of the patient, provisioning an intervention to the patient (e.g., based on the immune activation state), and/or any suitable steps.

The system and/or method can function to prepare a sample for measurement and/or analysis, measure properties of a sample, determine an immune activation state of a patient, and/or can otherwise function. In a specific example, the system and/or method can be used in an emergency department (e.g., of a hospital), urgent care, and/or doctor's office to triage patients (e.g., diagnose, determine a probability of, etc. a patient is experiencing a condition such as a sepsis-related condition). Examples of immune activation states include: sepsis (e.g., septicemia), sepsis-related condition, anemia, bleeding conditions, systemic inflammatory response syndrome (SIRS), blood cell health, organ health, cancer condition (e.g., metastatic cancer), inflammation, cytokine release (e.g., cytokine storms), autoimmune disorders (e.g., rheumatic disorders such as arthritis, lupus, etc.), graft-versus-host disease, and/or any suitable immune activation state or other health state. The immune activation state can be caused by and/or include a diagnosis of (e.g., a probability that the immune activation state is caused by) one or more pathogens (e.g., bacteria, virus, fungi, chemicals, etc. such as class of pathogen, specific pathogens, etc.) and/or other causes of the immune activation state. The immune activation state can be a binary state (e.g., yes or no whether the patient is positive for a given state), a severity index (e.g., 'healthy,' 'no indications,' 'mild,' 'moderate,' 'severe,' 'critical,' 'acute,' life-threatening,' etc.), a numerical value, a probability and/or likelihood that the patient has a condition, and/or other representation of an immune activation state.

2. Benefits.

Variations of the technology can confer several benefits and/or advantages.

First, variants of the technology can improve a reproducibility, repeatability, and/or a reliability of blood sample preparation for measurement and/or analysis. The enhanced reproducibility and/or reliability can be across different practitioners, different medical practices, different geographical areas, different times (e.g., hours, days, weeks, months, years, etc.), different systems, and/or in any suitable conditions. For example, standardizing the sample preparation procedure (e.g., using the same or same type of sample preparation module), determining optimal timings (e.g., process durations, relative timings, amount of time between processes, total process time, etc.), and/or determining preferred conditions (e.g., humidity, temperature, reagent concentration, reagent addition rate, reagent identity, etc.) can enable the technological advantage of improved reproducibility and/or reliability. For instance, the system and/or method can achieve a reproducibility of 1.0 score units (e.g., where the score can range from about 0 to 10, 0 to 100, and/or have any suitable range), where the score can be associated with an immune activation state. In another illustrative example, the system and/or method can achieve a reproducibility of at least 10% (e.g., 0.01%, 0.05%, 0.1%, 0.5%, 1%, 5%, 10%, values therebetween, etc.) in measurement of a biophysical parameter for a sample in different conditions. However, the system and/or method can achieve any suitable reproducibility and/or reliability.

Second, variants of the technology can decrease an incidence of user error (which can improve a reliability, repeatability, reproducibility, validity, etc. of the results). For example, automating most or all steps and/or sample interactions can reduce user interactions with the sample (which can also be beneficial for reducing an exposure risk of the user to the patient's blood sample).

However, variants of the technology can confer any other suitable benefits and/or advantages.

As used herein, "substantially" or other words of approximation (e.g., "about," "approximately," etc.) can be within a predetermined error threshold or tolerance of a metric, component, or other reference (e.g., within 0.001%, 0.01%, 0.1%, 1%, 5%, 10%, 20%, 30%, etc. of a reference), or be otherwise interpreted.

3. System.

Figure 14:
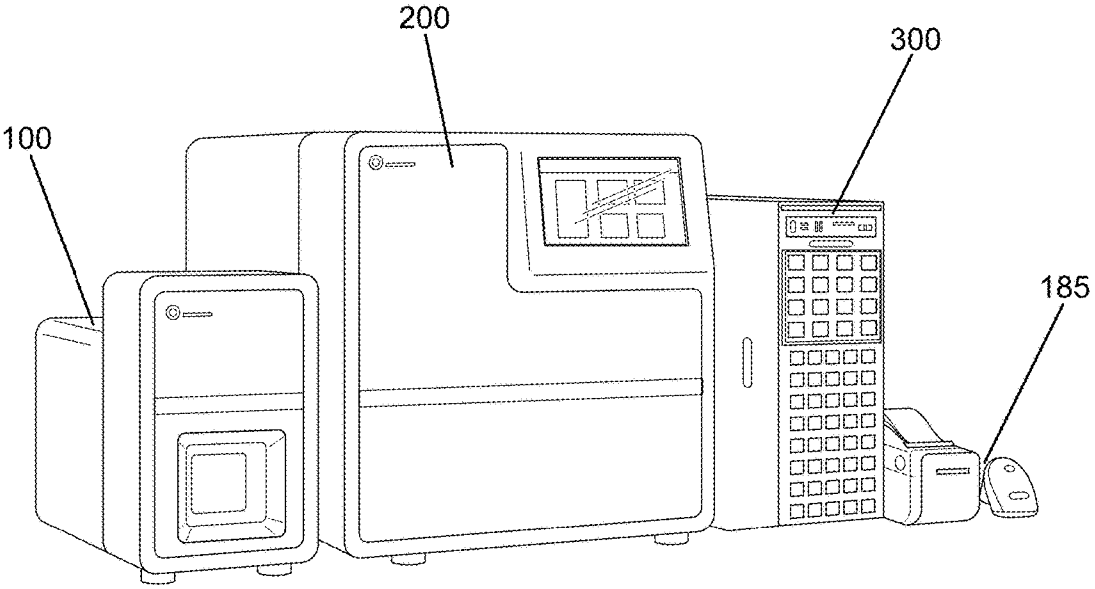
FIG. 14 is a schematic representation of an example of the system.

As shown in FIG. 1, the system can include a sample preparation module, a measurement module, a computing system, and/or any suitable components. The sample preparation module, measurement module, computing system, and/or other components can be integrated into a common housing (e.g., enclosure, unit, etc.), in separate housings and/or units (e.g., as shown for example in FIG. 14), two or more components can share a common housing, and/or the components can be integrated or connected in any manner.

The system preferably functions to prepare a sample (e.g., blood sample) for measurement, measure the sample, analyze the sample (e.g., to determine a patient health state, determine a patient immune activation state, etc.), and/or can otherwise function.

The sample preparation module 100 (e.g., sample preparation system, sample preparation subsystem, blood sample system, etc.) preferably functions to prepare a sample of a patient to be measured. The sample preparation module can additionally and/or alternatively function to store a sample (e.g., prepare a blood sample for storage, modify a blood sample to increase a lifetime, etc.) and/or can otherwise function. The sample 15 preferably refers to a blood sample associated with a patient (e.g., arterial sampled blood, venipuncture sampled blood, peripheral blood sample, fingerstick blood sample, venous blood, capillary blood, red blood cells, white blood cells, platelets, serum, plasma, etc.), but can additionally or alternative include mucus sample, urine sample, saliva sample, sputum sample, feces, semen, and/or other bodily fluids. The sample can be provided in a centrifuge tube (e.g., microcentrifuge tube), test tube, vacutainer tube, vials, well plates (e.g., 24 well plates, 48 well plates, 96 well plates, 384 well plates, standard well plates, deep-well plates, etc.), and/or any suitable container or receptacle. The sample receptacle 17 can be made of glass, plastic, metal, and/or any suitable material. The sample receptacle can have a diameter (e.g., maximum diameter, minimum diameter, average diameter, diameter proximal a center, opening diameter, etc.) that is between about 10 mm and 50 mm (e.g., 15 mm, 16 mm, 17 mm, 20 mm, 21 mm, 25 mm, 30 mm, 35 mm, 40 mm, 45 mm, etc.), a diameter less than about 10 mm, or a diameter greater than about 50 mm.

The sample preparation module is preferably autonomous (e.g., functions without user interaction, robotic, etc.), but can be semi-autonomous (e.g., require user engagement to move between one or more steps) and/or manual (e.g., require user input to perform one or more step such as adding reagents). For example, a user can load a sample in the sample preparation module and thereafter the sample preparation module can perform preparation steps without further user interaction. In another example, a user can perform a blood draw for a patient and the sample preparation module can automatically load and process the blood sample from the drawn blood. However, the sample preparation module can otherwise be automated.

Inputs to the sample preparation module include: a sample, a lysis solution, a quench solution, a buffer solution, a wash solution, fixing solution, staining solution, and/or any suitable solution(s) or inputs. The output of the sample preparation module can include a prepared sample 16, waste (e.g., byproducts from the lysis, quench, wash, etc. such as cell fragments, proteins, plasma, salts, residual reagents, etc.), and/or any suitable outputs. The output sample (e.g., residual material that is not degraded or removed from the sample) is preferably in substantially the same activation state as before being isolated and/or prepared (e.g., biophysical properties of the processed sample are the same as; within a threshold of; differ by less than about 15%, 10%, 5%, 2%, 1%, 0.5%, 0.1%, values therebetween, <0.1%, etc. relative to the biophysical properties of the same species before processing steps; etc.). The biophysical properties can include: cell subpopulations, relative amounts of cellular subpopulations, cell mechanical properties, cell size, cell shape, cell deformability, cell response to force (e.g., stress, strain, compression, expansion, etc.), trajectory (e.g., within a microfluidic chip), and/or any suitable properties. However, the output sample can be in a different activation state from the original sample, and/or can have any suitable state. As an illustrative example, an input sample can be a blood sample associated with a patient and an output of the sample preparation module can be a white blood cell sample (e.g., the red blood cells, platelets, etc. can be removed from the blood sample). In this specific example, processing the blood sample does not substantially change the activation state of (e.g., biophysical properties of) the white blood cells. However, the sample preparation system can receive any suitable inputs and/or outputs.

Figure 13:
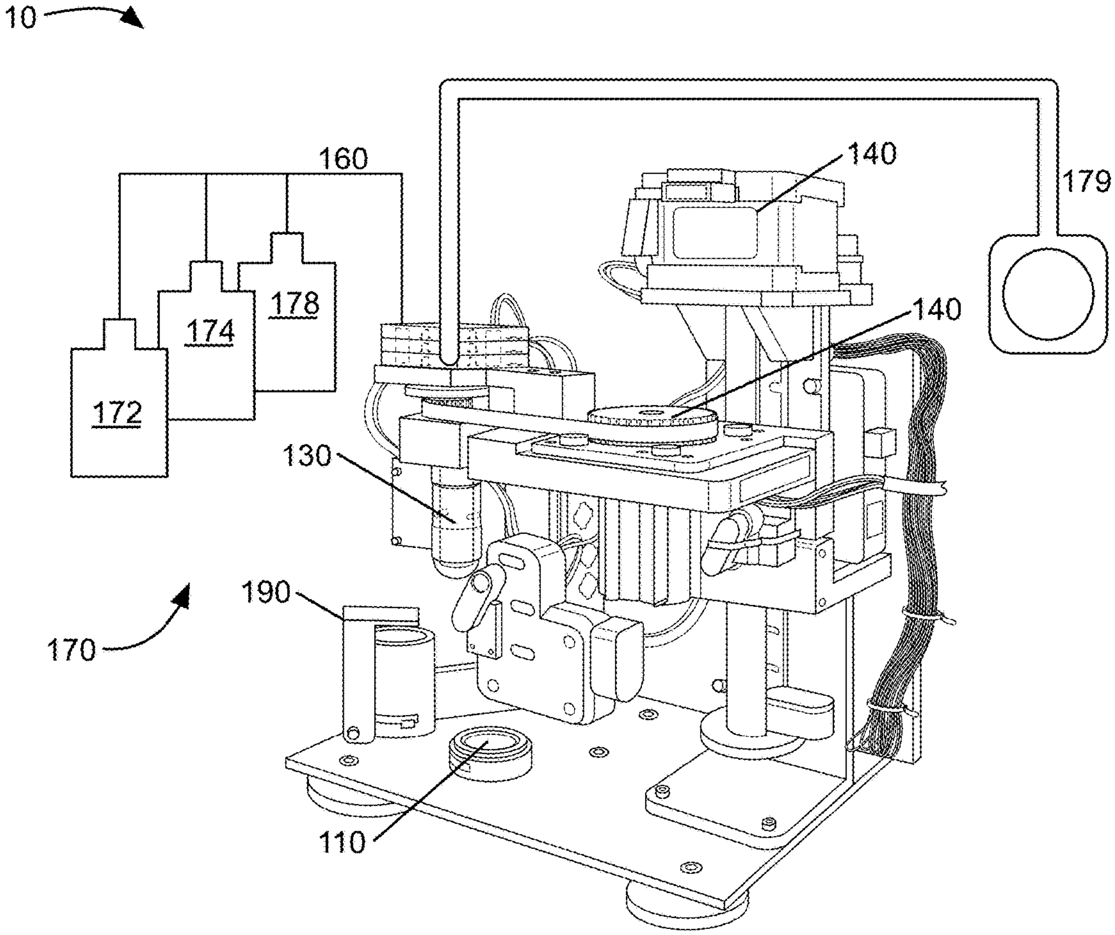
FIG. 13 is a schematic representation of an example of a sample preparation module.

As shown for example in FIG. 13, the sample preparation module can include: a sample holder, a reagent port, a spindle, a temperature control system, sensors, manifolds, reagent reservoirs, motor (e.g., stepper motor, centrifuge, etc.), and/or any suitable components.

The sample holder no preferably functions to support the sample within the sample preparation system. The sample holder can include (e.g., be) a test tube holder (e.g., a test tube rack, a ring with a diameter that matches a central diameter of the sample receptacle, etc.), clamps (e.g., finger clamps, ring clamps, etc.), tongs, and/or any suitable sample holder. The sample (e.g., sample receptacle) can be suspended in the sample holder, rest on a surface (e.g., curved surface that matches a curvature of the sample receptacle), and/or otherwise the sample can otherwise be held by the sample holder. The sample holder is preferably connected to a motor (e.g., such that the sample holder can be translated relative to other components of the system). The sample holder is preferably arranged under the spindle (e.g., centered under the spindle), but can have any suitable orientation relative to the spindle. The sample holder can optionally be connected to a mixer and/or agitation mechanism (e.g., magnetic stirrer, shaker, etc.).

The sample holder can include an automatic sampler, which can function to automatically load, change, unload, and/or otherwise automatically modify samples. For example, an automatic sampler can include a sample carousel (e.g., configured to retain a plurality of patient samples such as for a single patient, for a plurality of patients, etc. where the samples can include a label, position, holder, or other identifier to identify and coordinate sample transfer, process, etc.), robotics (e.g., configured to transfer a sample between a carousel and a sample holder), and/or any suitable automatic sampler can be included.

Figure 15:
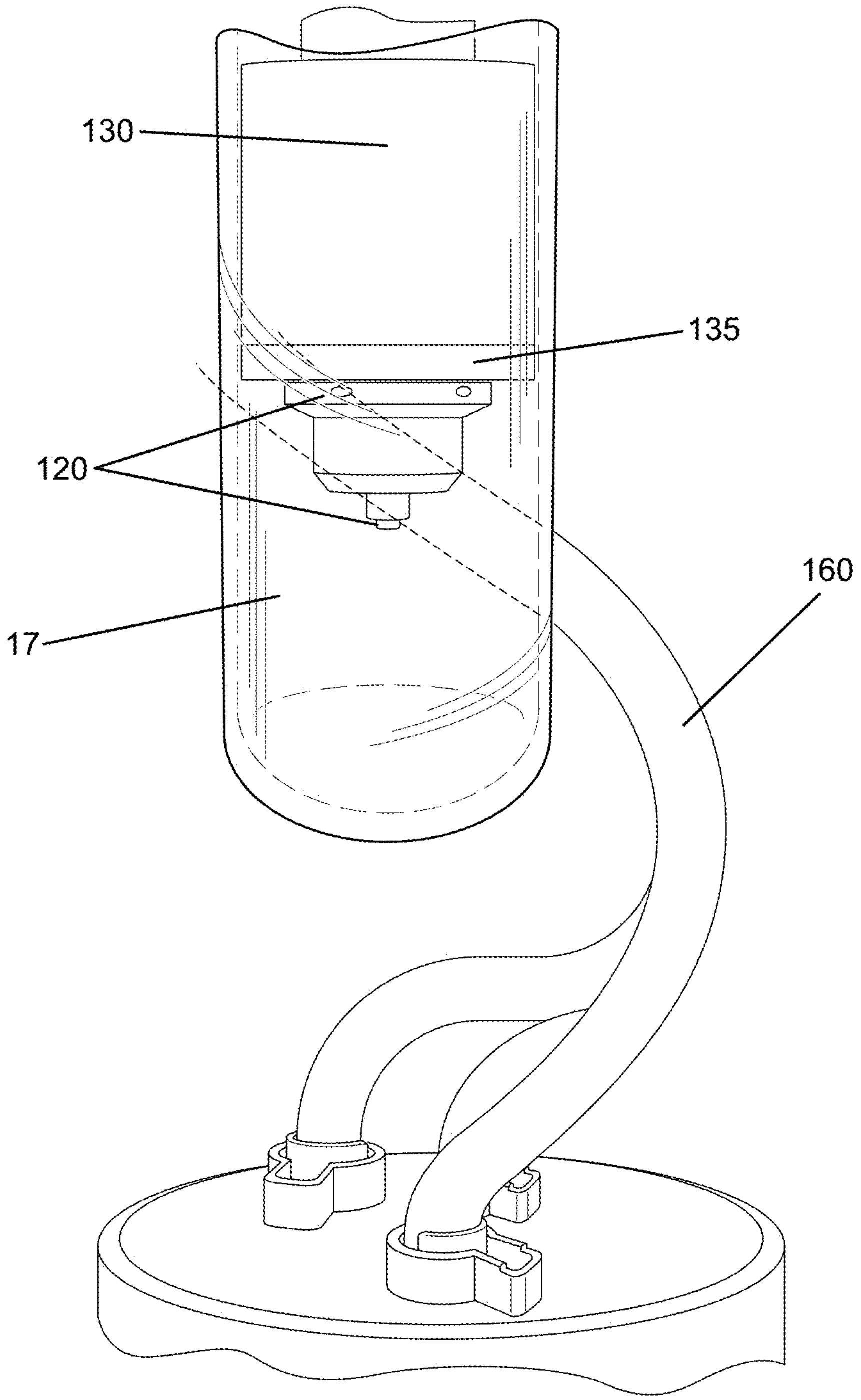
FIG. 15 is a schematic representation of an example of a sample holder interfacing with a spindle.

In some variations, the sample holder can be the same as (e.g., integrated into) the spindle and/or reagent port(s) (as shown for example in FIG. 15).

The reagent port 120 can function to introduce reagents into the sample, remove reagents from the sample (e.g., aspirate the sample), mix the sample, and/or can otherwise function. The reagent port preferably has a diameter smaller than the sample receptacle (e.g., so that the reagent port can fit inside the sample receptacle), but can have a diameter that is larger than and/or equal to the sample receptacle diameter. The reagent port can include a needle, tube, manifold, piping, and/or any suitable port can be used.

During operation, the reagent port is preferably inserted into the sample receptacle. The reagent port can be inserted fully, to a threshold height (e.g., above the sample, relative to the sample holder, relative to a top of a sample holder, relative to a bottom of a sample holder, etc.), to a minimum depth (e.g., flush with the receptacle entrance), submerged into the sample (e.g., to a threshold depth such as to cover one or more orifices with sample), and/or to any suitable depth. However, the reagent port can additionally or alternatively remain outside the sample receptacle (e.g., where different reagent ports can be used to introduce different reagents), and/or otherwise be arranged relative to the sample. When the system is not operating, the reagent port is preferably arranged above the sample holder (e.g., such that the port only needs to translate in one axis to enter a sample), but can have any suitable arrangement (e.g., require translation in 2 or 3 axes to access the sample).

The reagent port preferably includes a set of orifices (e.g., openings, holes, etc.) at the end (e.g., end inserted into the sample receptacle), where the orifices can enable reagents to be added to and/or removed from the sample. The orifices can share a common manifold (e.g., where the manifolds can split and/or connect to different end points) and/or be connected to different manifolds (e.g., each manifold connected to different reagents or end points). As an illustrative example, an orifice can be used to introduce lysing reagents, quenching reagents, washing reagents, buffer, water, fixing agents, vacuum (e.g., connected to a vacuum pump 179 such as to produce a vacuum pressure that is <10 mTorr, 10 mTorr, 20 mTorr, 50 mTorr, 100 mTorr, 150 mTorr, 200 mTorr, 300 mTorr, 400 mTorr, 500 mTorr, boo mTorr, 700 mTorr, 710 mTorr, 720 mTorr, 750 mTorr, 755 mTorr, 760 mTorr, values or ranges therebetween, etc.), and/or any suitable reagent(s).

Figure 4:
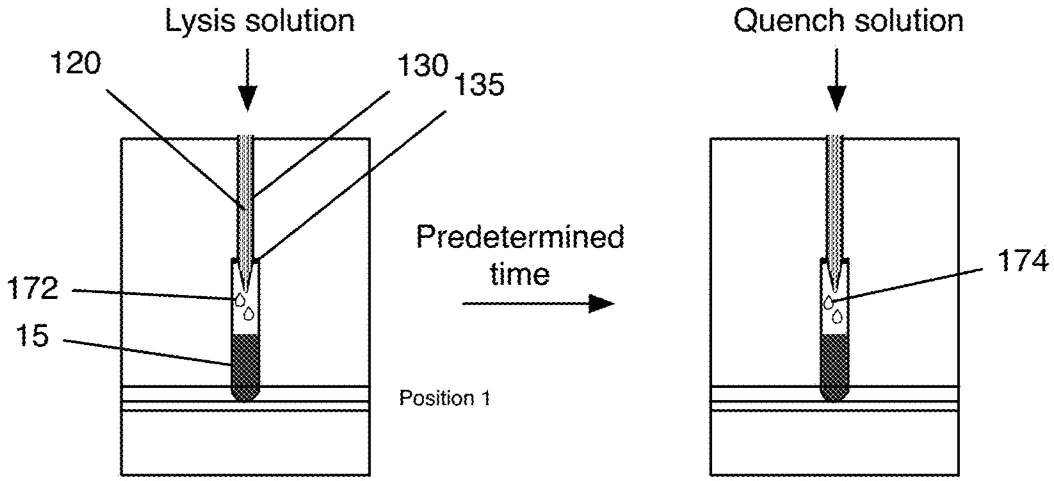
FIG. 4 is a schematic representation of an example of lysing and quenching a blood sample.
Figure 5:
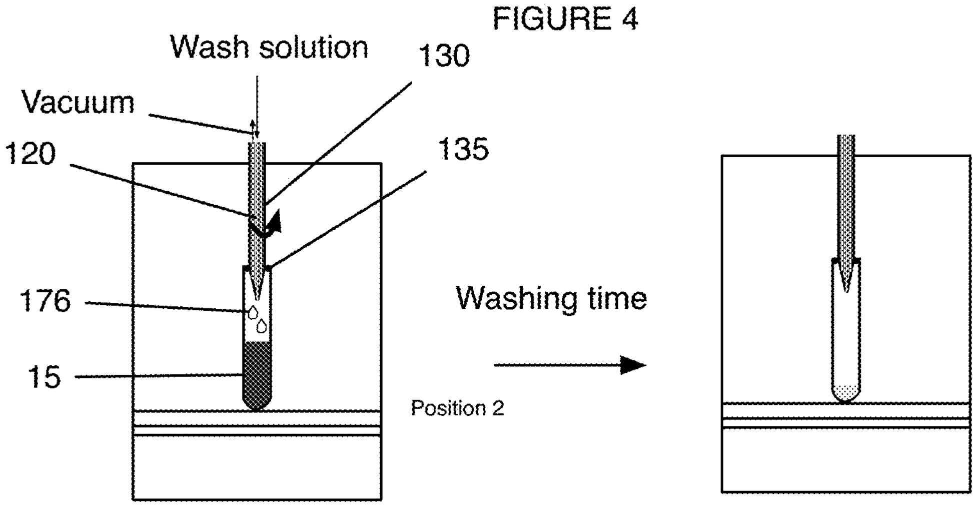
FIG. 5 is a schematic representation of an example of washing a lysed blood sample.
Figure 6:
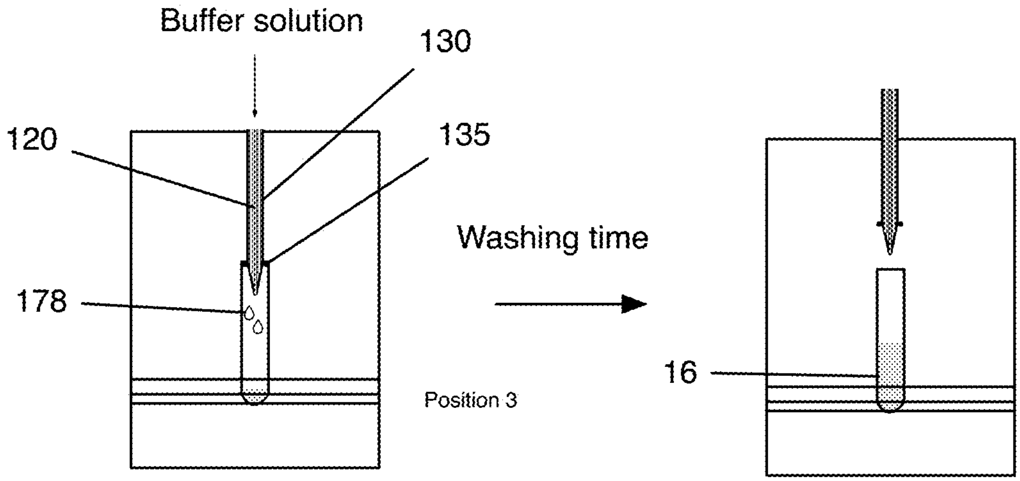
FIG. 6 is a schematic representation of an example of suspending the washed white blood cells.

In some embodiments, the reagents introduced using the orifices can depend on a motor position and/or sample holder position (e.g., height). For instance, an orifice can be open and/or closed depending on a position, a valve or other component function can depend on (e.g., via an interlock, switch, etc.) a sample position, an orifice can form a closed fluidic path depending on position (e.g., tubing can line up, and/or the orifices can otherwise depend on a motor and/or sample holder position. For example, as shown in FIG. 4, at a first height, the reagent port can introduce lysing reagents and/or quenching reagents. At a second height, as shown for example in FIG. 5, the reagent port can introduce washing reagents and vacuum (e.g., concurrently, contemporaneously, simultaneously, sequentially, according to a predetermined pattern, etc.). At a third height, as shown for example in FIG. 6, the reagent port can be used to introduce a buffer solution (e.g., to dilute the sample). However, the reagent port can additionally and/or alternatively perform these operations at the same height (e.g., at predetermined times) and/or in any suitable conditions.

Figure 3:
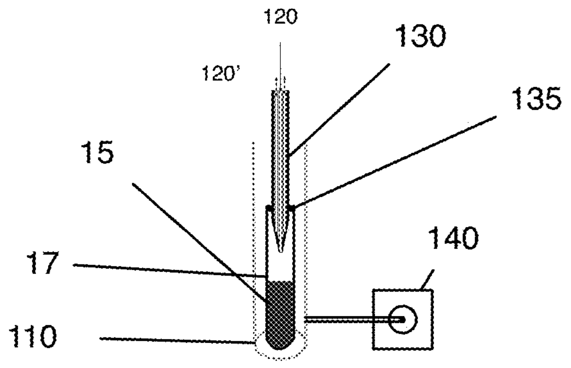
FIG. 3 is a schematic representation of an example of a blood sample on a sample holder (e.g., before processing).

The reagent port can include a plurality of through manifolds (e.g., separate fluid pathways as shown for example in FIG. 3), where each internal manifold can be connected to a separate endpoint (e.g., waste collection, vacuum, different reagents, etc.). However, the endpoint (or path to the endpoint) can be split (e.g., include valves, distributors, connectors, etc. that allow multiple endpoints to use a single manifold or reagent port) and/or can otherwise be configured.

In some variants, the system can include separate reagent ports. For example, a different reagent port can be used for each reagent, for subsets of reagents (e.g., reagents introduced before centrifuging, reagents introduced while centrifuging, reagents introduced after centrifuging), and/or to introduce any suitable reagents.

The spindle 130 preferably functions to centrifuge the sample, which is beneficial for separating species of the sample (e.g., based on solubility, density, mass, etc.). For example, a blood sample can be centrifuged (e.g., after hemolysis) to concentrate white blood cells and remove red blood cell fragments.

The spindle is preferably the same as the reagent port (e.g., cooperatively integrated parts), but can be separate from the reagent port.

The sample is preferably centrifuged with a relative centrifugal force between about 500-5000 g, but can be centrifuged at less than 500 g and/or greater than 5000 g. For example, the sample can be centrifuged at about 8000 rpm (e.g., in an approximately 15 mm diameter sample container such as 8000±1000 rpm).

The spindle preferably includes a seal 135 (e.g., adhesive, gasket, chemical, screw, mechanical sealant, etc.) which functions to connect and/or seal the spindle and the sample (e.g., to enable a vacuum to be drawn, to prevent sample from evacuating the sample receptacle, etc.). The seal is preferably reversible, but can be irreversible. For example, a gasket (e.g., a rubber gasket, o-ring, etc.) can be inflated and/or deflated to seal and unseal the connection, a snug fit (that can be overcome with a force in the opposite direction), a threaded seal, and/or any suitable seal can be used.

The reagent reservoirs 170 (e.g., bottles, containers, etc.) preferably function to store reagents to be dispensed and/or used for the sample preparation. The reagent reservoirs can be located within a housing (e.g., a sample preparation system housing), outside of the housing (e.g., outside the sample preparation system housing), and/or in any suitable location. The reagent reservoirs are preferably coupled through a manifold (e.g., tubing) to the sample preparation system (e.g., reagent ports, spindle, sample, etc.), but can be directly feed into (e.g., be gravity coupled) and/or otherwise be coupled to the sample preparation system. The reservoirs can be closed and/or open to an external environment. The reservoirs can be made of glass, plastic, metal, and/or any suitably compatible material.

The reagents in the reservoir(s) are preferably premade (e.g., include a mixture of reagents for a given processing step, a separate reservoir for each process, etc.). However, additionally or alternatively, a separate reservoir can be present for each component of a reagent and/or reaction process, and/or the reservoirs can otherwise include any suitable reagents. In a first specific example, a lysis reservoir can include a prepared lysis solution 172. In a second specific example, a first reservoir can include formic acid (e.g., for lysis) and a second reservoir can include a buffer solution (e.g., where the formic acid and buffer solution can be mixed (e.g., in a mixing chamber, in a manifold, etc.) and/or aliquoted (e.g., to achieve a target concentration) to form the lysis solution in situ, within the manifold, and/or at any suitable location.

For example (e.g., as shown in FIG. 13), a sample preparation system can include a lysis reagent reservoir (e.g., that contains lysing reagents 172), a quenching reagent reservoir (e.g., that contains quenching reagents 174), a washing reservoir (e.g., that includes or contains washing solution 176), and/or a buffer reservoir (e.g., that includes or contains a buffer reagent 178). However, the sample preparation system can include any suitable reservoirs.

The manifold(s) 160 function to transfer one or more reagents between endpoints. The manifolds can operate under positive and/or negative pressure. The manifolds are preferably include (e.g., are made of) chemically compatible materials (e.g., plastics, metals, glass, etc. that do not react with reagents that intentionally, incidentally, etc. contact the material), but can include weakly-compatible (e.g., compatible for a threshold duration of contact, compatible to a threshold concentration of reagent, etc.) and/or non-compatible materials. Each reservoir can have a separate manifold, the manifolds can meet (e.g., at a connector, valve, distributor, etc.), the reservoirs can share manifolds (e.g., where one or more manifolds can be closed to enable selective reagent uptake), and/or the manifolds can otherwise be configured. In a specific example, each reservoir can include a manifold (e.g., tubing) configured to uptake reagent(s) from the reservoir. In this specific example, the manifolds can be connected or combined (e.g., using a splitter, valve, multiport connector, etc.) where reagents from a single manifold can be added (e.g., via a reagent port, spindle, etc.) at a time (e.g., a single manifold is fluidly coupled to the sample at a time). However, the manifolds can otherwise be configured.

The motor 140 preferably functions to move (e.g., spin, move, translate, rotate, etc.) the sample. The motor can move the sample directly (e.g., be directly connected to the sample) and/or indirectly (e.g., via intermediate components). The motor can be connected to the sample, the sample holder, the spindle, the manifolds, the sensors, the cleaning bath, and/or to any suitable component(s). Exemplary motors can include: brushed motors (e.g., DC brushed motors, AC brushed motors, etc.), brushless motors (e.g., brushless DC motors, brushless AC motors, etc.), switched reluctance motors, universal motors, induction motors, hysteresis motors, pancake motors, stepper motors, and/or any suitable motor(s).

The sample preparation system can include more than one motor. For example, a stepper motor can be used to set a sample height (e.g., adjust a height of, translate, etc. a sample, sample holder, spindle, etc.) and a DC motor can be used to centrifuge the sample (e.g., spin the sample via the spindle). However, any suitable motors can be used for any suitable purpose.

The temperature control system 150 of the sample preparation system preferably functions to maintain a temperature of the sample within the sample preparation system at or about a target sample temperature. The target sample temperature is preferably about 25° C. (e.g., 25±1° C., 24-26° C., 20-30° C., 25±0.5° C., 21-29° C., 22.5-27.5° C., etc.), but can be less than about 25° C. (e.g., 0° C., 5° C., 10° C., 15° C., 20° C., values therebetween, etc.) and/or greater than about 25° C. (e.g., 30° C., 35° C., 37° C., 38° C., 39° C., 40° C., 45° C., values therebetween, etc.). The temperature control system can include heaters (e.g., radiative heaters, convective heaters, conductive heaters, resistive heaters, gas heaters, etc.) and/or coolers (e.g., air conditioners, peltier coolers, heat sinks, thermoelectric cooler, absorption coolers, compression coolers, etc.). The temperature control system can be in direct contact with components (e.g., touching a sample receptacle, touching a manifold, touching a spindle, integrated in a spindle, integrated in a sample holder, integrated in a sample receptacle, etc.), indirectly contact components (e.g., include an air gap between the heater and/or cooler and the component, include a thermally conductive material between the heater and/or cooler, etc.), be isolated from components (e.g., to prevent heating or cooling of one or more components such as by having a thermally isolating material between the component and the heater and/or cooling unit) and/or can otherwise be arranged.

The temperature can be actively controlled (e.g., using a positive feedback loop, negative feedback loop, based on sensor readings, using PI control, PD control, PID control, etc.) and/or passively controlled.

Figure 7:
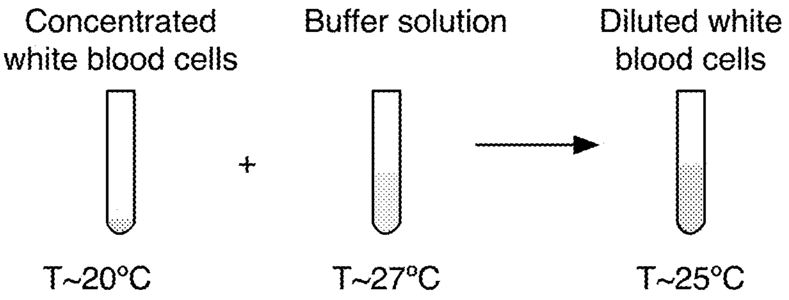
FIG. 7 is a schematic representation of an example of suspending the white blood cells to achieve a target temperature after the suspension.

In a first illustrative example, an environment within the sample preparation system can be maintained at about the target sample temperature. In a second illustrative example, the sample can be maintained at the target sample temperature. In a variation of the second illustrative example, the sample and the reagents (e.g., reservoirs, manifolds, etc.) can be maintained at the target sample temperature. In a third illustrative example, a temperature of one or more component and/or reagent can be controlled to modify the sample temperature to maintain about the target sample temperature. For instance (as shown in FIG. 7), when a temperature of the sample is about 20° C., a temperature of a reagent (e.g., lysis reagent, quenching reagent, buffer, diluent, etc.) can be set to about 27° C. so that the final sample temperature (e.g., after mixing) is 25° C. The specific temperatures of each component can be measured, determined empirically, determined heuristically, determined according to an equation (e.g., a thermal mass balance), and/or can otherwise be determined. The temperature of the reagent can be set in the reservoir, in the manifold, in the reagent port, in the spindle, and/or can be set at any suitable location within the sample preparation system. However, the temperature of any suitable component(s) can be controlled in any manner.

The sensor(s) 180 can function to measure one or more aspects (e.g., parameters, properties, etc.) of a sample in the sample preparation system. Exemplary aspects include: mass, volume, temperature, height (e.g., height relative to other components, total height within a sample receptacle, etc.), color, density, degree of lysis, activation state, pressure, and/or any suitable aspects. The aspects can be measured continuously, intermittently, at predetermined times, at predetermined frequencies, at specified times during operation of the system, and/or with any suitable timing. The sensor(s) can be integrated into the components (e.g., spindle, manifold, reagent port, sample receptacle, sample holder, motor, etc.), be directed toward the other components (e.g., spindle, manifold, reagent port, sample receptacle, sample holder, motor, etc.), and/or can otherwise be arranged inside or outside of the sample preparation system.

Exemplary sensors include: optical sensors (e.g., cameras, lasers, interferometers, etc.), acoustic sensors, pressure sensors, rulers, ultrasonic sensors, depth sensors (e.g., RADAR, LIDAR, SONAR, depth cameras, stereocameras, etc.), spectrometers, scanners 185 (e.g., to scan a patient identification associated with the sample, to scan a cartridge lot, to scan a reagent tag, to facilitate or speed up data entry, to ensure accurate data entry, etc.), and/or any suitable sensor(s) can be used.

The sample preparation system can optionally include a washing unit 190. The washing unit preferably functions to wash the sample preparation system (e.g., the spindle, reagent ports, etc.). For example, after a sample has been prepared, the washing unit can be used to wash the sample preparation system (e.g., the spindle, reagent port, etc. thereof) before another sample is prepared. However, the washing unit can be used with any suitable timing. As shown for example in FIG. 13, the washing unit can be translated (and/or rotated) out of the way for a sample to be loaded, and can then be positioned in the sample location after a sample has been prepared.

The washing unit can, for example, be an empty sample receptacle, an empty container, a filled container, and/or any suitable container. The washing unit can be filled (e.g., via reagent port, spindle, manually, etc.) with a washing reagent (e.g., buffer, surfactant, soap, etc.) and treated in the same manner as a sample, can be treated to one or more washing steps (e.g., including agitation, wash solution addition, buffer addition, centrifuging, spinning, mixing, aspiration, etc.), and/or can otherwise be treated to wash the sample preparation system and/or components thereof. The washing unit is preferably integrated into the sample preparation system, but can be separate from the sample preparation system (e.g., to be manually inserted such as by a user before and/or after preparing a sample). The sample preparation system is preferably washed automatically, but can be washed manually, semiautomatically, and/or with any suitable responsiveness. The sample preparation system is preferably washed after each use, but can be washed after a predetermined number of uses, before each use, at a predetermined frequency, based on a need for washing (e.g., how dirty the sample preparation system is), according to a washing schedule, and/or with any suitable timing.

The measurement module 200 preferably functions to measure one or more sample parameters (e.g., sample properties). The measurement module preferably operates on a prepared sample (e.g., a sample that has been prepared by a sample preparation system), but can operate on an unprepared sample and/or on any suitable sample. The samples can be transferred automatically (e.g., using a robotic arm, using an automated pipette, etc.), manually (e.g., by a user), and/or otherwise be transferred from the sample preparation system to the measurement module.

The sample properties can include: individual properties (e.g., properties of individual cells), aggregate properties (e.g., combinations of properties of individual cells such as portrayed by a distribution, an average property, a median property, modal property, $95^{th}$ percentile value, etc.), bulk properties (e.g., properties of the sample as a whole such as density, optical absorption, etc.), and/or any suitable properties.

Exemplary sample properties can include: structural parameters, trajectory parameters, patient parameters, location parameters (e.g., cell position relative to the image frame, relative to the channel, relative to the outlet, relative to the inlet, relative to the stagnation point, etc.), and/or any parameters. Examples of structural parameters include: shape (e.g., ellipticity, helicity, oblongness, circularity, curvature, skewness, etc.), aspect ratio (e.g., ratio of longest dimension to shortest dimension, ratio of length to width, etc.), size (e.g., lateral extent, longitudinal extent, depth, height, width, length, volume, surface area, etc.), constituent structure (e.g., cell membrane location, cell shape, cell wall structure, etc.), constituent morphology (e.g., cell morphology, cell shape, particle shape, etc.), internal structure (e.g., shape, morphology, size, etc. of a nucleus and/or other organelle of a cell), and/or any other structural parameters. Examples of patient parameters include: complete particle count, complete blood count, complete leukocyte count, complete neutrophil count, complete monocyte count, complete lymphocyte count, complete basophil count, complete eosinophil count, complete erythrocyte count, complete platelet count, constituent numerosity (e.g., number of cells and/or segments of cells, number of particles and/or segments of particles, etc.), presenting symptoms (e.g., patient temperature, blood pressure, weight, blood oxygenation, etc.), cell density, cell culture results, hydration, and/or any other sample parameters.

Figure 12:
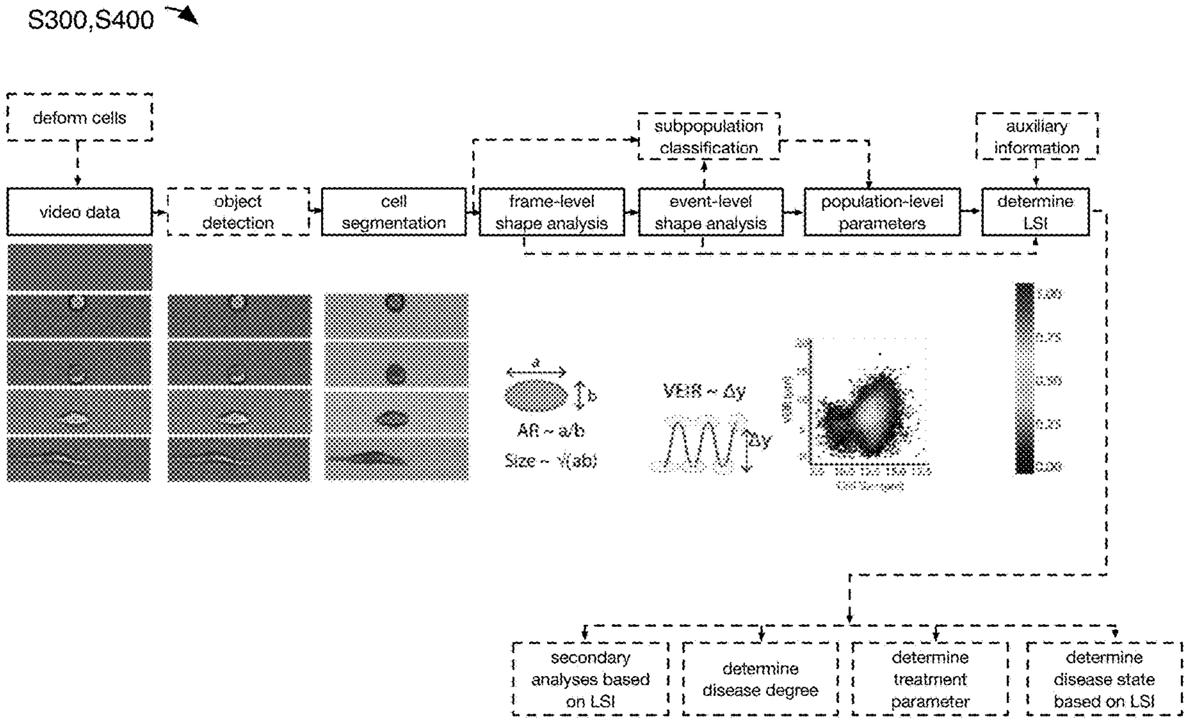
FIG. 12 is a schematic representation of an example of determining a biophysical parameter and/or immune activation state of a patient.

Trajectory parameters can be parameters that are associated with and/or determined from the trajectory of the cell through the microfluidic cartridge (e.g., the deformation region of the microfluidic cartridge, the focusing region, etc.). The trajectory can be a series of discrete positions (e.g., of the centroid, of the center of mass, of a reference point, average position of the cell, etc.) of the cell, a continuous path of the cell, and/or correspond to any motion of the cells as they pass through the fluid flow (e.g., deformation region of the microfluidic cartridge). Examples of trajectory parameters include: direction of object and/or feature motion, speed of object and/or feature motion (e.g., average speed, instantaneous speed, etc.), acceleration of object and/or feature motion, an oscillation in the object and/or feature motion (e.g., an amplitude of the oscillation, a frequency of the oscillation, a phase of the oscillation, a modulation in the oscillation, a decay of the oscillation, as shown for example in FIG. 12, etc.), visco-elastic inertial response (VEIR), a deviation in the particle flow trajectory (e.g., from a linear path, an expected path, etc.), and/or any other trajectory parameters. The trajectory parameters can be determined based on a difference, sum, amplitude, maximum, minimum, average value of, and/or other characteristic of one or more positions of the trajectory. In variations where the trajectory parameters include an oscillation, the oscillation can correspond to an oscillation of a reference point (e.g., centroid, extrema, etc.), a reference axis (e.g., one or more dimension such as length, width, depth), one or more reference surface (e.g., object boundary, interior boundary of the object such as corresponding to an organelle boundary, etc.), reference volume (e.g., object volume, internal structure of the object, etc.), and/or other portion of the object. The oscillation preferably occurs along a reference axis perpendicular to the direction of motion of the object. However, the reference axis can be parallel to the direction of motion and/or have any orientation relative to the direction of motion. The oscillation amplitude is preferably on the micron-size scale (e.g., 1-10 μm, 10-100 μm, etc.), but can additionally or alternatively be nanometer scale (e.g., 1-100 nm, 100 nm-1 μm, etc.) and/or be any suitable distance.

However, any suitable sample properties can be measured.

The measurement module is preferably housed in a separated housing (e.g., unit, enclosure, as shown for example in FIG. 14, etc.) from the sample preparation module. However, the measurement module and sample preparation module can be housed in the same housing. The measurement module is preferably located within a threshold distance of the sample preparation module (e.g., on the same table, in the same room, within 1 m, 2 m, 5 m, 10 m, 20 m, 50 m, etc.), which can provide the technological advantages of ensuring that the temperature of the sample does not change significantly between sample preparation and sample measurement, facilitating rapid sample measurement, and/or can provide any suitable technical advantage.

In an illustrative example, the measurement module can be a cytometry module (e.g., a flow cytometry module), where the sample (e.g., prepared sample) can be loaded in a cytometry cartridge 210 (e.g., microfluidic device, microfluidic channel, channel, etc.). The measurement module can include: an imaging system 220, a motor 230, a temperature control system 240, vibration isolators 250, a pressure system 260, and/or any suitable components. However, the measurement module can additionally or alternatively include an atomic force microscopy module, an optical probe module, and/or any suitable module(s) and/or components.

The cartridge (e.g., cytometry cartridge) can function to receive the sample, sort the sample, apply a stimuli to the sample, and/or can otherwise function. The cartridge is preferably a single use cartridge (e.g., to reduce a risk of contamination between different samples), but can be a multiuse cartridge. The cartridge can be made of plastic, glass, metal, and/or any suitable materials.

Figure 8:
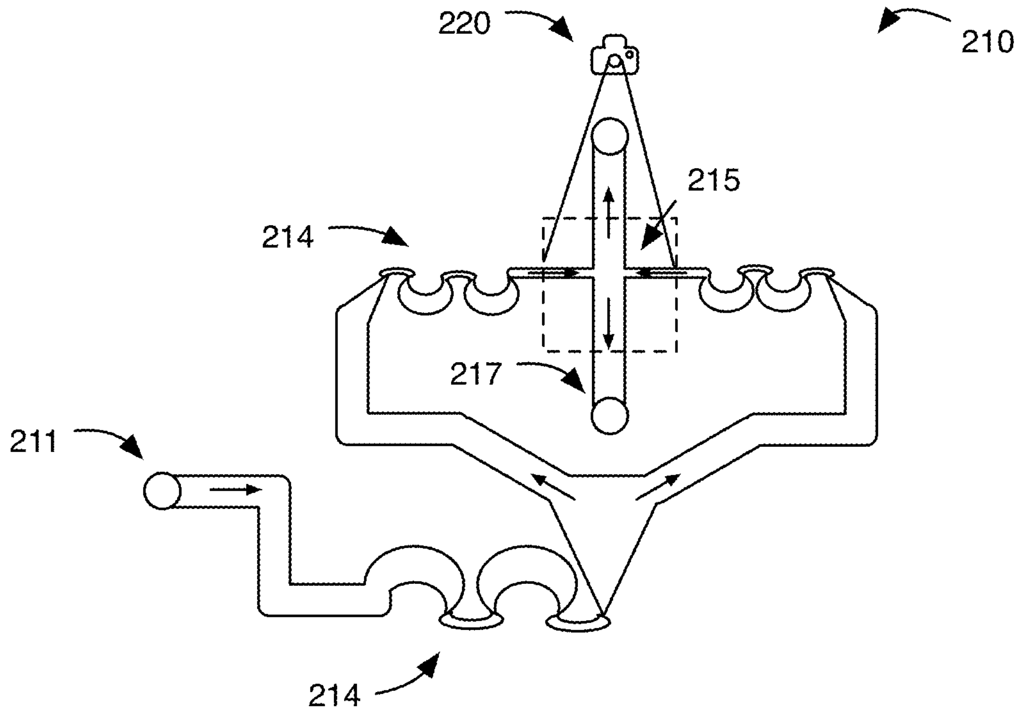
FIG. 8 is a schematic representation of an example microfluidic flow path.
Figure 16A:
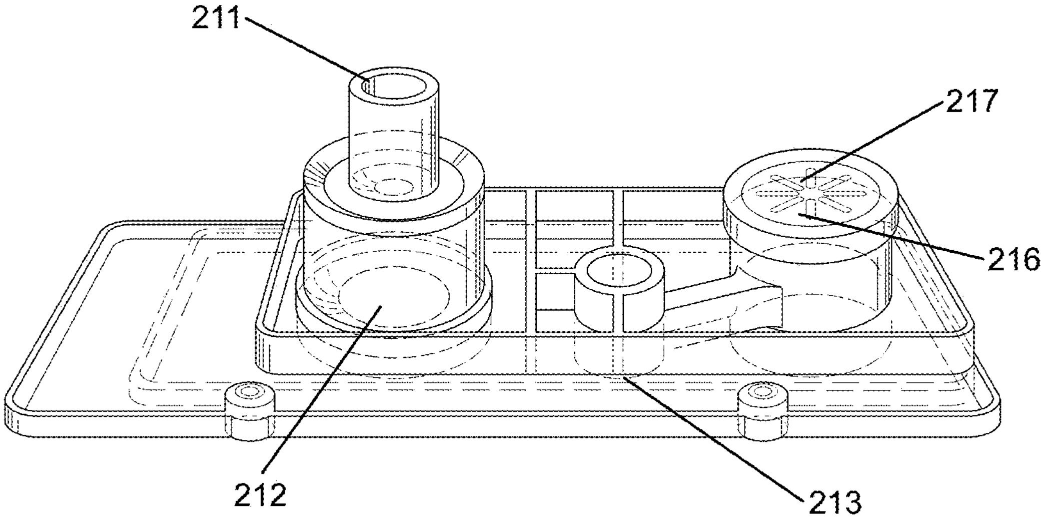
FIGS. 16A and 16B are schematic representations of an exemplary assembled cartridge and an exemplary microfluidic channel thereof, respectively.
Figure 16B:
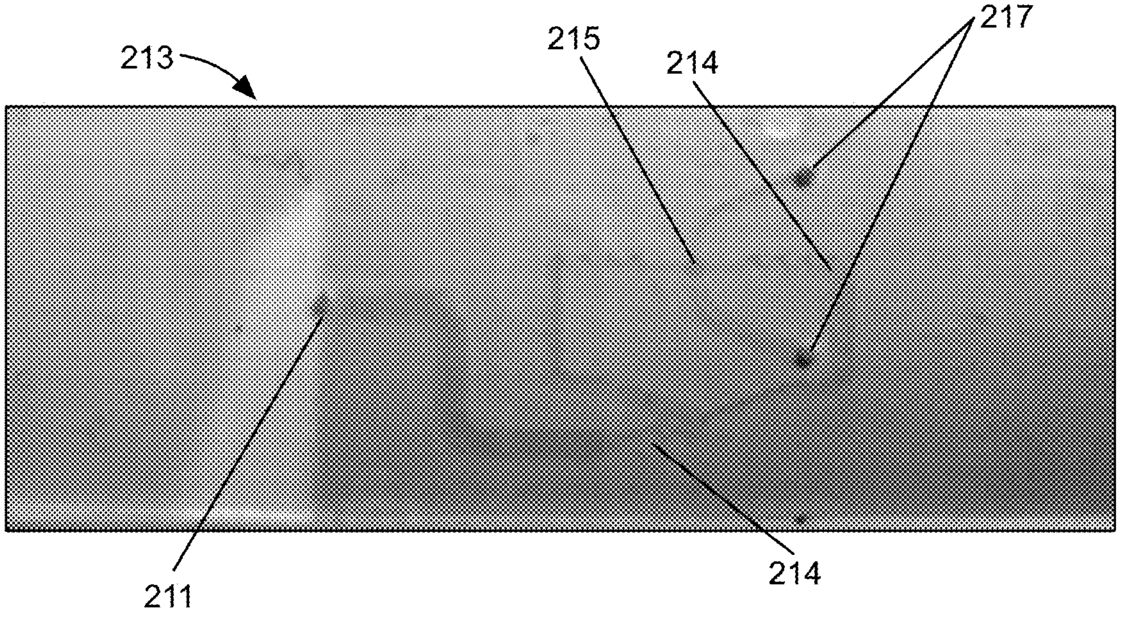

As shown for example in FIG. 16A, the cartridge can include an inlet 211, inlet filter 212, a microfluidic channel 213, an outlet filter 216, an outlet 217, and/or any suitable components. As shown for example in FIG. 8 and/or FIG. 16B, the sample can enter the cartridge through the inlet 211, pass through the inlet filter 212 (e.g., to remove particle clumps, to minimize a cross contamination within the measurement module, etc.), enter a focusing region 214 (e.g., of the microfluidic channel such as comprising a plurality of sharp bends or turns; which can function to sort the sample into individual constituents, focus the constituents into a path of the microfluidic device, etc.), enter a deformation region 215 (e.g., an extensional flow region such as comprising a first flow including the sample constituents and a second flow intersecting the first flow; which can function to apply a stress, strain, pressure, force, etc. to the sample), and exit through an outlet (e.g., via an outlet filter). However, the cartridge can otherwise be arranged. The intersection (e.g., of the deformation region) can be a three way intersection (e.g., a "T" junction, a "Y" junction, etc.), a two way intersection (e.g., an "L" junction, an "I" junction, a "V" junction, a venturi junction, etc.), a four way intersection (e.g., an "x" junction, a "t" junction, a "K" junction, etc.), and/or have any suitable geometry.

The cartridge is preferably loaded into a cartridge holder, which is configured to hold the cartridge (e.g., without enabling the cartridge to shift or move within the holder; with a threshold tolerance such as 0.0001", 0.0005", 0.001", 0.005", 0.01", 0.05", etc.; etc.).

In specific examples, the cartridge can include and/or be any suitable microfluidic system as disclosed in U.S. application Ser. No. 16/374,663 filed 3 Apr. 2019 and entitled 'SYSTEM AND METHOD FOR DEFORMING AND ANALYZING PARTICLES,' U.S. Application Ser. No. 15/868,025 filed 11 Jan. 2018 entitled 'METHOD AND DEVICE FOR HIGH THROUGHPUT CELL DEFORMABILITY MEASUREMENTS,' U.S. Application Ser. No. 16/676,352 filed 6 Nov. 2019 entitled 'METHOD AND DEVICE FOR HIGH-THROUGHPUT SOLUTION EXCHANGE FOR CELL AND PARTICLE SUSPENSIONS,' U.S. Pat. No. 9,464,977 filed 18 Oct. 2013 entitled 'SYSTEM AND METHOD FOR DEFORMING, IMAGING AND ANALYZING PARTICLES,' U.S. Pat. No. 10,252,260 filed 3 Apr. 2017 entitled 'SYSTEM AND METHOD FOR DEFORMING PARTICLES,' each of which is incorporated in its entirety by this reference.

Figure 9:
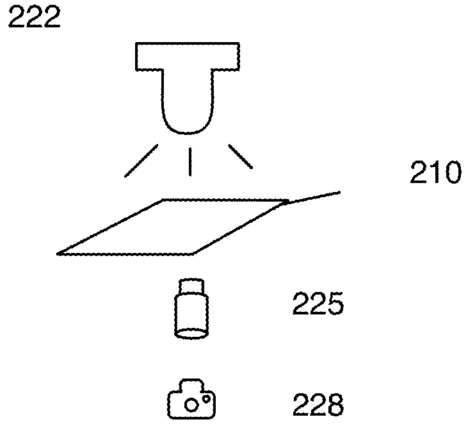
FIG. 9 is a schematic representation of an exemplary imaging system.

The imaging system preferably functions to acquire images of the sample (e.g., images of cells of the sample), where the images can be analyzed to determine the sample properties. The imaging system is preferably arranged around (e.g., above; below; next to; optically connected to such as via mirrors, optical fibers, free space coupling, optical materials, immersion oil, etc.; as shown for example in FIG. 9; etc.) the cartridge. However, the imaging system can otherwise be arranged.

The imaging system can include a lighting system 222, imaging optics 225, an image sensor 228, and/or any suitable components. The lighting system is preferably a light emitting diode (e.g., LED, which can be beneficial for introducing a relatively small amount of heat into the measurement module), but can additionally or alternatively include an incandescent light, a fluorescent light, a black light, a halogen lamp, and/or any suitable light source. The light source is preferably arranged for Köhler illumination of the sample (e.g., to generate an even illumination of the sample without producing an image of the illumination source in the resulting image; such as by including a collector lens and/or field lens, field diaphragm, condenser diaphragm, condenser lens, etc.; etc.), but can additionally or alternatively be arranged for critical illumination and/or in any suitable illumination. The light source can be above, below, and/or otherwise be arranged relative to the sample.

The imaging optics can include a microscope objective, a condenser, lenses, mirrors, polarizers, waveplates, and/or any suitable components. The imaging optics can be fixed (e.g., set to a fixed location relative to the sample) and/or moveable (e.g., moveable relative to the sample such as the optics can move and/or the sample can be moved to achieve a target focal plane). For example, the sample and/or optics can be translated (e.g., using a motor) to set a focus of the imaging optics on the sample (e.g., on a deformation region of the sample). In this example, a set of optical guides (e.g., on the cartridge) can be used to facilitate the focusing of and/or the alignment of the sample to the imaging system (e.g., imaging optics).

The image sensor is preferably a high speed camera (e.g., a camera able to acquire at least 1000 fps; 2000 fps; 5000 fps; 10,000 fps; 20,000 fps; 50,000 fps; 100,000 fps; 200,000 fps; 500,000 fps; 1,000,000 fps; values therebetween; >1,000,000 fps; etc.), but can be a low-speed camera (e.g., a camera able to acquire at most woo fps, 120 fps, 100 fps, 60 fps, 50 fps, 30 fps, 24 fps, 20 fps, 12 fps, values there between, <12 fps, etc.) and/or any suitable camera. The camera is preferably a visible camera (e.g., a CCD, CMOS, etc. such as able to detect at least 400-800 nm radiation), but can additionally or alternatively be sensitive to infrared radiation (e.g., near-IR, mid-IR, far-IR, etc.), ultraviolet radiation, x-ray, microwave, radio wave, and/or any suitable radiation. The image sensor can be arranged above, below, and/or with any suitable position or orientation relative to the sample (e.g., cartridge).

In an illustrative example, the imaging system can be (e.g., configured as) a microscope (e.g., upright microscope, inverted microscope, confocal microscope, etc.). However, any suitable imaging system can be used.

The temperature control system can function to preheat the cartridge (e.g., heat and/or cool the cartridge to achieve a target temperature before the addition of sample), maintain a temperature of the cartridge, maintain a temperature of the sample, maintain a temperature of the measurement module, and/or can otherwise function. The temperature control system can be localized (e.g., to a component of the measurement module) and/or global (e.g., effect, impact, etc. the entire measurement module). For example, the temperature control system can be integrated into a cartridge holder, a cartridge, an imaging system, a vibration isolation system, and/or into any suitable components. The temperature control system can be a radiative, nonradiative, convective, conductive, combination thereof, and/or any suitable temperature control system.

The temperature control system (e.g., of the measurement module) can include and/or be the same as and/or different from a temperature control system as described above for the sample preparation system. For example, a measurement module temperature control system can have a higher temperature tolerance (e.g., achieve, maintain, etc. a more accurate, precise, etc. temperature). For instance a sample preparation system temperature can be maintained with a tolerance of about ±i° C. and a measurement module temperature can be maintained with a tolerance of about ±0.3° C. However, the temperature tolerance of the measurement module can be the same as and/or less than the temperature tolerance of the sample preparation system.

The vibration isolators preferably function to dampen and/or minimize an impact of motion of the cartridge on an alignment of the cartridge. The vibration isolators are preferably connected to the cartridge (e.g., via the cartridge holder), but can be integrated into the cartridge, integrated into the cartridge holder, connected to the imaging system, connected to a housing of the measurement module, and/or can otherwise be connected and/or arranged. Exemplary vibration isolators include honeycomb structures, springs, pneumatic isolators, sheets or pads of flexible materials (e.g., rubber, elastomer, cork, foam, laminate, etc.), tuned mass dampeners, rope isolators, active vibration isolators (e.g., including a sensor such as a piezoelectric accelerometer, force sensors, MEM accelerometers, geophones, proximity sensors, interferometers, etc.; an actuator such as a linear motor, pneumatic actuator, piezoelectric motor, etc.; a controller; etc.), and/or any suitable vibration isolators can be used. The vibration isolator can dampen low frequency vibrations (e.g., <0.1 Hz, <1 Hz, <5 Hz, <10 Hz, etc.), middle frequency vibrations (e.g., 10-10000 Hz), high frequency vibrations (e.g., >10000 Hz), combinations thereof, and/or any suitable frequency vibrations. The vibration isolators can be horizontal isolators, vertical isolators, six-degrees of freedom isolators, three-degrees of freedom isolators, and/or isolate vibrations in any suitable axes or directions.

The motor preferably functions to translate the sample (e.g., cartridge) relative to the imaging system (e.g., to change a portion of the cartridge, sample, etc. within the field of view of, focal plane of, etc. the imaging system). However, the motor can otherwise function. The motor is preferably coupled to (e.g., connected to, mechanically coupled to, able to translate, etc.) the cartridge (e.g., cartridge holder), but can be coupled to the imaging system (e.g., light sources, optical components, image sensor, etc.), and/or to any suitable component. The motor can be continuously operable (e.g., set the position to an arbitrary position) and/or discretely operable (e.g., set the sample position to one or more discretized positions).

The sample can be stationary, translated, and/or otherwise be moving during measurements. For example, the sample can be moved at predetermined times, according to a movement schedule, to correct for vibrations, randomly (e.g., to isolate systematic movement errors, vibrations, etc.), and/or can otherwise be moved. In a specific example, after loading the sample can be aligned (e.g., moved) such that the deformation region of the cartridge is within the field of view of the imaging system. In a second specific example, the sample can be focused (e.g., by translating the sample along the optical axis of the imaging system). In a third specific example, before (or after) measuring images of the sample (e.g., cells within the deformation region), the sample can be translated so that the imaging system acquires a plurality of images of the sample at a location upstream of the deformation region. The images from the third specific example can be used to determine (e.g., measure, calculate, estimate, etc.) a flow rate of the sample (e.g., cells within the sample, fluid speed within the sample, etc.) and/or any suitable sample properties (e.g., cell mechanics in the absence of a deformation force, cell count, etc.). After the sample property is determined, the sample can be translated such that the deformation region is within the field of view of the imaging system. However, the sample properties (e.g., flow rate) can otherwise be determined. These specific examples are non-limiting and non-exclusive examples, the sample can be translated according to one or more of these examples in combination.

The pressure system preferably functions to urge the sample through the cartridge (e.g., through the microfluidic channel). The pressure system can be a positive pressure (positive displacement, such as to push the sample through) system, a negative pressure (e.g., negative displacement such as to pull the sample through) system, and/or any suitable combination thereof and/or type of displacement system. The pressure system is preferably connected to the cartridge (e.g., an inlet, outlet, etc. thereof), but can additionally or alternatively be connected to any suitable component. Exemplary pressure systems include: vacuum pumps, peristaltic pumps, syringe pump, microfluidic pump, microfluidic precision pump, and/or using any suitable pump. The pressure system preferably generates a pressure differential (e.g., between an inlet and outlet of the cartridge) that is approximately 90 psi (e.g., 90±1, 90±3, 90±5, 90±10, etc.), but can generate a pressure differential between about 50 and 150 psi, less than 50 psi, and/or greater than 150 psi. The pressure differential can depend on the target flow rate, the sample temperature, the sample viscosity, the sample pH, the sample Zeta potential, the average sample particle size, the channel size (e.g., nano-, micro-, milli-, etc. channel), and/or depend on any suitable property(s).

The computing system 300 can function to control the operation of the sample preparation system, control the operation of the measurement module, to process (e.g., analyze) the data (e.g., images) acquired by the measurement module, to determine a score (e.g., leukocyte structural index (LSI), sepsis, diagnostic score, probability of a diagnosis, etc.), and/or can otherwise function. The computing system can be local (e.g., a dedicated computer, as shown for example in FIG. 14, etc.), remote (e.g., cloud computing, server, database, etc.), and/or distributed in any manner (e.g., the sample preparation system can include a computing system, the measurement module can include a computing system, a dedicated processing computing system can be included, etc.). The computing system can include one or more: processors, microprocessors, computer processing units, graphics processing units, and/or any suitable processors. In a specific example, the computing system can include a GPU accelerated computation, which can be beneficial for rapidly and/or efficiently handling (e.g., processing) large datasets (such as generated by image sets).

The computing system can include an image analyzer 320 which can function to determine sample properties (particularly but not exclusively mechanical properties and/or trajectory parameters) from the set of images. The image analyzer can include a segmentation module (e.g., which can function to segment the images into a foreground such as cell(s) and a background), a feature module (e.g., which can function to identify or determine a feature of the image such as a cell centroid, cell boundary, cell edge, cell membrane, etc.), a positioning module (e.g., to determine a position of a feature within the image), a processing module (e.g., which can function to determine sample properties based on the position, feature shape, feature shape evolution, position evolution, etc.), and/or any suitable components. The image analyzer can include a machine learning algorithm, stereoscopic algorithms (e.g., optic flow), classifier, and/or any suitable algorithms and/or equations. The image analyzer can process individual images (e.g., frame-level analysis such as to determine cell properties within a given frame), set of images (e.g., event-level analysis such as to track a cell as it moves through the deformation region, field of view, etc.), population analyses (e.g., to process the sample as a whole), and/or any suitable analysis.

The image analyzer can include a quality detector 325 which can function to determine a quality (e.g., a score, a ranking, use versus don't use, etc.) of the images, where the quality of the images can be used to determine whether an image should be analyzed or included in the analysis. The quality can be a frame-level, event-level, population-level, and/or any suitable level quality. For example, an image with a low quality can be excluded from the set of analyzed images, can exclude images within a threshold number of frames from the set of analyzed images, can exclude images that include the same features (e.g., the same cells) from the set of analyzed images, and/or can otherwise be used to modify which images are analyzed. In specific examples, the quality can depend on the number of cells in the image(s), an overlap of cells in the image (e.g., low quality when cells are touching and/or overlapping, high quality when the cells are separated), a distance between the cells, and/or the quality can be derived from the cells in any suitable manner.

The computing system can include a scoring module 340 which can function to use the sample properties (e.g., determined by the image analyzer) to determine a diagnostic score (e.g., LSI, probability of diagnosis, diagnosis, etc.) associated with a sample (and/or patient). The scoring module can include one or more equations, machine learning algorithms (e.g., neural networks, convolutional neural networks, recurrent neural networks, etc.), classifiers, look-up tables, statistical regressions, Bayesian regressions, and/or any suitable method to determine the score. Inputs to the scoring module can include: sample properties, patient information (e.g., patient demographics, patient presenting symptoms, etc.), one or more images (e.g., average images, representative images, all images, images of cells at or near particular positions of the cartridge, etc.), ambient conditions (e.g., temperature, humidity, pressure, etc.), flow rate, sample temperature, and/or any suitable inputs. The output of the scoring module can be a score (e.g., a numerical score; a numerical value such as 0-1, 0-10, 1-10, 0-100, 1-100, etc.; etc.), a classification (e.g., "low-probability of sepsis", "medium probability of sepsis", "high probability of sepsis", "further testing recommended", "other diagnostic tests recommended", "sepsis treatment recommended", etc.), color coded information (e.g., green such as to indicate low probability of sepsis, low probability of dangerous immune activation state, etc.; yellow such as to indicate further testing required, that the results were inconclusive, etc.; red such as to indicate a high probability of sepsis, high immune activation, etc.; etc.), and/or any suitable information.

The computing system (e.g., the image analyzer, the scoring module, etc.) can be trained using a set of training data (e.g., labeled training data, unlabeled training data, etc.). The set of training data preferably includes data associated with patients diagnosed with a high immune activation state (e.g., have sepsis, have metastatic cancer, have cancer, etc.) and data associated with patients diagnosed with a low immune activation state (e.g., do not have sepsis, do not have metastatic cancer, do not have cancer, etc.). However, the training data set can include any suitable data.

In some embodiments, the computing system (e.g., the image analyzer and/or the scoring module in isolation or combination) can perform any suitable operations and/or methods as disclosed in U.S. patent application No. 17/401,627, titled "SYSTEM AND METHOD FOR IMMUNE ACTIVITY DETERMINATION" filed on 13 Aug. 2021, and incorporated in its entirety by this reference. However, the computing system can otherwise operate.

4. Method.

As shown in FIG. 2, the method can include preparing a sample and measuring the sample. The method can optionally include: pretreating the system (or portions thereof), determining an immune activation state of the patient, provisioning an intervention to the patient (e.g., based on the immune activation state), and/or any suitable steps.

The method is preferably performed by a system (e.g., as described above), but can be performed by any suitable system. In some embodiments of the method (and/or steps thereof), timing can be beneficial for achieving accurate, reproducible, reliable, valid, and/or other qualities results (e.g., diagnoses). For example, the duration of steps, amount of time between steps (e.g., maximum amount of time, minimum amount of time, etc.), total amount of time the method is performed, amount of time preparing the sample, amount of time measuring the sample, amount of time analyzing the measurements of the sample, and/or any suitable timing can enable technical advantages of the method. In some embodiments of the method (and/or steps thereof), the temperature (e.g., of the sample, of the system, of system components, etc.) can be beneficial for achieving accurate, reproducible, reliable, valid, and/or other qualities results (e.g., diagnoses). For example, maintaining a temperature of the sample at a target temperature during sample preparation, during sample storage (e.g., before, during, and/or after sample preparation or measurement), during sample measurement, and/or at any suitable time can help ensure that measured data is of sufficient quality. These embodiments can be related, combined, separate, and/or otherwise be related or not related. However, the method may, in some situations, provide results (e.g., with a sufficient quality) without (or with less stringent control over) the timings, temperature, and/or other suitable properties.

The method preferably minimizes user input and/or feedback which can be beneficial for ensuring that the method is performed consistently for different samples. For instance, the steps of the method can be performed automatically, can include checks to ensure that steps are being performed properly, and/or can otherwise be performed. However, the method and/or steps thereof can be performed with input and/or feedback from a user. In a specific example of the method, a user can load a sample into a sample preparation module (e.g., for sample preparation) and/or can transfer the prepared sample to a measurement module (e.g., to be measured), where other method steps in this example can be performed without user intervention (e.g., the method can run upon closing the sample preparation module, upon closing the measurement module, etc.). However, the sample can be added automatically (e.g., using a robotic arm, an autosampler, an automatic pipette, etc.), can be transferred automatically (e.g., using a robotic arm, an autosampler, an automatic pipette, etc.), a user can activate one or more method steps, and/or can otherwise perform steps of the method.

Pretreating the system S100 preferably functions to prepare the system to receive a sample. Pretreating the system can be particularly beneficial for ensuring that the system is within target conditions for operation. Pretreating the system can include pretreating a sample preparation module, pretreating a measurement module, and/or pretreating any suitable components. Pretreating the system can be performed concurrently with (e.g., contemporaneously with, simultaneously with, etc.) preparing the sample, before preparing the sample, and/or after preparing the sample (e.g., before measuring the sample).

Pretreating the system can include: loading a cartridge (e.g., into a measurement module), heating (and/or cooling) the cartridge to a target temperature, washing the sample preparation system (e.g., processing a buffer solution, processing a washing solution, etc.), washing the measurement module, processing a calibration sample (e.g., a sample with particles of known properties, a sample with fixed cells, etc.), pretreating (e.g., diluting, heating, cooling, adding anticoagulant, fixing, etc.) the sample, setting environmental conditions of the sample preparation module (e.g., temperature, pressure, humidity, etc.), setting environmental conditions of the measurement module (e.g., temperature, pressure, humidity, etc.), cooling an imaging system, and/or any suitable steps. In a specific example, the cartridge can be loaded into the measurement module before a sample can be introduced into the sample preparation system, which can be beneficial for enabling the cartridge to be aligned to the imaging system, preheat the cartridge (e.g., to a target temperature, to a stabilized temperature, etc.), and/or can otherwise be beneficial. However, pretreating the system can include any suitable steps.

Preparing the sample S200 preferably functions to prepare the sample for measurement. The sample is preferably prepared using a sample preparation module, but can be prepared by a user and/or by any suitable system. The sample is preferably prepared before the sample is measured. However, the sample can be prepared at the same time as (e.g., the sample can be measured while it is being prepared) and/or after the sample is measured (e.g., the sample can be postprocessed after measurement, processing can be used to measure sample properties, etc.).

Between about 0.1 and 10 mL of sample is preferably prepared (e.g., transferred to the sample preparation system). For example, about 1 mL (e.g., 1 mL±10%) of sample can be transferred. In this example, when more or less sample is provided to the sample preparation system (e.g., less than 900 μL, greater than 1.1 mL, such as resulting from user error, pipette error, etc.), a new sample can be loaded (e.g., the user can be instructed to discard the sample and load a new on), the processes can be adjusted to account for the volume (e.g., increase and/or decrease reagents, time, speeds, etc. based on the loaded volume), the sample can be processed as normal (e.g., including a flag indicating that the results derived therefrom may not be conclusive as a result), and/or the processes can otherwise be modified and/or remain the same.

Preparing the sample can including: lysing the sample S220, quenching the sample S240, washing the sample S260, suspending the sample S280, and/or any suitable processes.

Lysing the sample preferably functions to degrade red blood cells (e.g., erythrocytes) and/or other cells (e.g., cells other than leukocytes, cells that are not to be measured, etc.) from the sample (e.g., haemolysis, hemolysis, etc.). Lysing the sample preferably does not change an activation state and/or any properties of the species (e.g., cells, leukocytes, white blood cells, etc.) to be measured, which can be beneficial for ensuring that the measurements are representative of the sample state. However, lysing the sample can change an activation state and/or properties of the species to be measured (e.g., by a known amount, in a known way, to effect a predetermined change, to remove one or more subpopulations of leukocytes, to remove a subpopulation of species, etc.).

Lysing the sample preferably includes adding a lysing solution to the sample and mixing (e.g., stirring, agitating, etc.) the sample, but can additionally or alternatively include heating the sample, sonicating the sample, irradiating the sample, and/or any suitable processes.

The lysing solution can include: lysing reagent(s) (e.g., cell membrane disruptor, detergents, etc.; which can function to lyse the species; such as formic acid, ammonium chloride, CTAB, diethylene glycol, saponin, etc.), anticoagulant(s) (e.g., functional to prevent clotting, aggregation, etc.; such as sodium EDTA, heparin, warfarin, sodium citrate, acid-citrate-dextrose, citrate, oxalate, batroxobin, hementin, vitamin E, alcohol, coumarins, etc.), surfactant (e.g., functional to modify a surface tension of the lysing solution; such as phosphotidyl choline, sophorolipid, rhamnolipid, lecithin, bile salts, etc.), fixing agent (e.g., functional to preserve species and/or subspecies of the sample; such as formaldehyde, paraformaldehyde, glutaraldehyde, phenol, etc.), solvent (e.g., water; saline water; sea water; buffer such as potassium bicarbonate, buffered saline, phosphate-buffered saline (PBS), tris-buffered saline (TBS), borate buffered saline, tris-NaCl-Tween buffer (TNT), phosphate buffered Tween (PBT), HEPES, sodium acetate, cacodylate, citrate, Sorensen's phosphate buffer, "Good" buffers, 4-(2-hydroxyethyl)-1-piperazineethanesulfonic acid (HEPES) buffer, phosphate citrate buffer, tris buffer, barbital buffer, etc.; etc.), staining agent (e.g., contrast agent, fluorescent dyes, phosphorescent dyes, etc.), and/or any suitable components. The lysing solution preferably includes mild reagents, but can include harsh reagents, corrosive reagents, and/or any suitable reagents. In a specific example, the lysing solution can include 1-5% (e.g., by weight, by volume, by composition, etc.) formic acid solution (e.g., in water, in buffer, etc.). Variations of the specific example can include saponin (e.g., 0.1%-1% saponin concentration by weight, by volume, by composition, etc.) and/or not include saponin (e.g., be composed essentially of a solution that does not have saponin or other terpenoids). However, any suitable lysing solution can be used.

Lysing the sample can use (e.g., in one or more aliquots or additions) between about 0.1 ml and 100 ml of lysing solution (e.g., 0.1 ml, 0.2 ml, 0.5 ml, 1 ml, 2 ml, 5 ml, 10 ml, 20 ml, 50 ml, 100 ml, values or ranges therebetween, etc.).

The sample is preferably lysed for a lysing time. The lysing time can depend on the amount of sample, the sample temperature, the lysing solution (e.g., concentration, reagents, constituents, etc.), the sample type, the quenching solution, the quenching mechanism, the measurement module (e.g., the type of measurements to be performed), the target sample (e.g., properties of the target sample), and/or can otherwise be determined. The lysing time is preferably between about 5 seconds and 60 seconds (e.g., 5 s, 10 s, 15 s, 20 s, 25 s, 30 s, 35 s, 40 s, 45 s, 50 s, 55 s, 60 s, values therebetween, etc.). When the lysing time is too long, white blood cells (or other species to be measured) can change their activation state, be lysed, and/or can otherwise be changed or impacted. When the lysing time is too short, the red blood cells can be incompletely lysed (e.g., and therefore can be difficult to separate), and/or the sample can otherwise be incompletely processed. However, the lysing time can be less than 5 seconds and/or greater than 60 seconds. In a specific example, the lysing time can be about 10 seconds (e.g., 9-11 s, 6-12 s, 9.5-11.5 s, 5-15 s, 6-14 s, 8-12 s, 9.5-10.5 s, 5-30 s, etc.). However, the lysing time can be any suitable time.

The sample can be lysed at ambient temperature (e.g., room temperature, environment temperature, 15-25° C., etc.), at an elevated temperature (e.g., about 25° C., 30° C., 35° C., 40° C., 45° C., etc.), at a depressed temperature (e.g., about 0° C., 10° C., 15° C., etc.), and/or at any suitable temperature.

Quenching the sample preferably functions to quench (e.g., stop, halt, slow, etc.) the lysing reaction. The sample is preferably quenched before the species to be measured have been lysed or otherwise impacted by the lysis process. However, the sample can be lysed after the species to be measured have been impacted. For instance, the sample can be quenched immediately (e.g., within at most 1 s, 2 s, 5 s, 10 s, 20 s, etc.) after the lysis time has elapsed. However, the sample can be quenched concurrently with the lysis (e.g., the quenching can occur via diffusion rather than mixing) and/or with any suitable timing.

Quenching the sample preferably does not change an activation state and/or any properties of the species (e.g., cells, leukocytes, white blood cells, etc.) to be measured, which can be beneficial for ensuring that the measurements are representative of the sample state. However, quenching the sample can change an activation state and/or properties of the species to be measured (e.g., by a known amount, in a known way, to effect a predetermined change, to remove one or more subpopulations of leukocytes, to remove a subpopulation of species, etc.).

Quenching the sample preferably includes adding a quenching solution to the sample and mixing (e.g., stirring, agitating, etc.) the sample, but can additionally or alternatively include heating the sample (e.g., to burn off lysing reagents, to evaporate the lysing agents, etc.), cooling the sample, sonicating the sample, irradiating the sample, and/or any suitable processes. The quenching solution can depend on the sample (e.g., volume, concentration, identity, species, etc.), the lysing solution (e.g., concentration, lysing reagent, etc.), temperature, humidity, pressure, and/or on any suitable sample or environment properties. Quenching the sample can use (e.g., in one or more aliquots or additions) between about 0.1 ml and 100 ml of quenching solution (e.g., 0.1 ml, 0.2 ml, 0.5 ml, 1 ml, 2 ml, 5 ml, 10 ml, 20 ml, 50 ml, 100 ml, values or ranges therebetween, etc.).

The quenching solution is preferably a basic solution (e.g., a buffered solution with pH greater than 7, a solution with a pH greater than the lysis solution, etc.), but can be an acidic solution and/or neutral solution. For example, the quenching solution can include quenching agent such as a carbonate (e.g., carbonate of sodium, lithium, potassium, rubidium, caesium, beryllium, magnesium, calcium, strontium, barium, aluminium, etc.), bicarbonate (e.g., bicarbonate of sodium, lithium, potassium, rubidium, caesium, beryllium, magnesium, calcium, strontium, barium, aluminium, etc.), acetate (e.g., acetate of sodium, lithium, potassium, rubidium, caesium, beryllium, magnesium, calcium, strontium, barium, aluminium, etc.), salt(s) (e.g., sodium chloride, sodium sulfate, etc.), and/or any suitable quenching species. The quenching agent can be dissolved in water, saline, buffer, solvent (e.g., alcohol, ether, glycol, solvent mixture, etc.), and/or in any suitable solvent(s). As an illustrative example, the quenching solution can include a 1-10% sodium bicarbonate solution (e.g., in water, in buffer, etc.). The quenching solution can exactly neutralize the lysis solution, over neutralize the lysis solution (e.g., the remaining solution can have residual quenching agents), and/or under neutralize the lysis solution (e.g., the remaining solution can have residual lysis reagents).

The sample is preferably quenched (e.g., mixed, quenching agent present for, etc.) for a quenching time. The quenching time can depend on the amount of sample, the sample temperature, the lysing solution (e.g., concentration, reagents, constituents, etc.), the quenching solution (e.g., concentration, reagents, constituents, etc.), the sample type, the quenching mechanism, the measurement module (e.g., the type of measurements to be performed), the target sample (e.g., properties of the target sample), and/or can otherwise be determined. The quenching time is preferably between about 5 seconds and 60 seconds (e.g., 5 s, 10 s, 15 s, 20 s, 25 s, 30 s, 35 s, 40 s, 45 s, 50 s, 55 s, 60 s, values therebetween, etc.). When the quenching time is too long, white blood cells (or other species to be measured) can change their activation state, be lysed, and/or can otherwise be changed or impacted. When the quenching time is too short, the lysing solution or reagents thereof can be insufficiently quenched allowing the lysis to continue, and/or the sample can otherwise be incompletely processed. However, the quenching time can be less than 5 seconds and/or greater than 60 seconds. In a specific example, the quenching time can be about 10 seconds (e.g., 9-11 s, 6-12 s, 9.5-11.5 s, 5-15 s, 6-14 s, 8-12 s, 9.5-10.5 s, 5-30 s, etc.). However, the quenching time can be any suitable time.

The sample can be quenched at ambient temperature (e.g., room temperature, environment temperature, 15–25° C., etc.), at an elevated temperature (e.g., about 25° C., 30° C., 35° C., 40° C., 45° C., etc.), at a depressed temperature (e.g., about 0° C., 10° C., 15° C., etc.), and/or at any suitable temperature.

Washing the sample preferably functions to remove particle debris from the sample, to isolate the species of the sample to be measured from byproducts or other sample components, to remove lysis and/or quenching byproducts, and/or can otherwise function. The sample is preferably washed within a threshold time after the sample has been quenched. For example, the sample can be washed immediately (e.g., within 1 s) after the quenching time has elapsed. In another example, the sample can be washed within a threshold time (such as 1 s, 2 s, 5 s, 10 s, 20 s, 30 s, etc.) of the quenching time elapsing. However, the sample can be washed after than sample has been quenched (e.g., a delay can be introduced between quenching the sample and washing the sample), and/or the sample can otherwise be washed.

Washing the sample can include: introducing a washing solution S262, agitating the sample S264, collecting the sample S266, aspirating the sample S268, decanting the sample, and/or any suitable steps and/or processes.

The washing solution is preferably a buffer solution, but can be a water, saline, include solvents (e.g., ether, alcohol, etc.), and/or any suitable solvent and/or solution. The washing solution can be added all at once, in aliquots, dropwise (e.g., slowly), and/or in any suitable manner. In some variants, the washing solution can be added concurrently (e.g., contemporaneously with, simultaneously with, etc.) aspirating the sample. However, washing the sample can include alternating adding washing solution, agitating (e.g., mixing) the sample, and aspirating the sample, and/or the sample can be washed in any manner. Washing the sample can use (e.g., in one or more aliquots or additions) between about 1 ml and 100 ml of washing solution (e.g., 1 ml, 2 ml, 5 ml, 10 ml, 20 ml, 50 ml, 100 ml, values or ranges therebetween, etc.).

Collecting the sample preferably functions to separate the prepared sample into sample to be measured (e.g., subspecies of the sample) and sample constituents to be discarded (e.g., waste, byproducts, degradants, residual reagents, etc.). The sample constituents to be measured are preferably retained (e.g., collected), but can be used in any manner. The sample constituents to be discarded are preferably discarded (e.g., into a waste process), but can additionally or alternatively be measured (e.g., using a separate measurement module, to acquire auxiliary data for the analysis, etc.), and/or used in any manner.

Collecting the sample preferably includes centrifuging the sample. The sample can be centrifuged using a microcentrifuge, low-speed centrifuge, high-speed centrifuge, ultracentrifuge, and/or any suitable centrifuge. For example, the spindle can be used to centrifuge the sample. The centrifuge can be used as a fractionation centrifuge, differential centrifuge, density gradient centrifuge, and/or in any suitable centrifugation process. The sample can be centrifuged at a rate that sediments the constituents to be measured, that does not sediment the constituents to be discarded, that does not substantially change an activation state of the constituents, that does not damage the constituents, based on a centrifuging duration (e.g., an amount of time necessary to sediment the constituents), and/or at any suitable rate. For example, the sample can be centrifuged at a rate that generates a relative centrifugal force between about 500-5000 g (e.g., a rate that is approximately 1000-20000 RPM). In this example, the sediments (e.g., pellet) preferably include the sample constituents to be measured (e.g., leukocytes) and the supernatant includes the sample constituents to be discarded (e.g., lysed erythrocytes). However, the pellet can include the sample constituents to be discarded, the supernatant can include the sample constituents to be measured, the sample can be segregated into a plurality of fractions (e.g., erythrocytes, buffy coat, plasma, etc.), and/or the sample can be separated in any suitable manner. However, the sample can be centrifuged at a rate that generates a relative centrifugal force less than 500 g and/or greater than 5000 g. However, collecting the sample can additionally or alternatively include: sedimenting the sample (and/or constituents), precipitating the sample (and/or constituents), and/or any suitable process.

After centrifuging the sample, the supernatant is preferably removed. The supernatant is typically discarded, but can be stored, processed, measured, and/or otherwise handled. The supernatant can be removed by decanting, aspirating, flicking, harvesting, and/or using any suitable technique.

The total washing time is preferably between about 5 s and 120 s (e.g., 5 s, 10 s, 15 s, 17 s, 20 s, 23 s, 30 s, 35 s, 45 s, 60 s, 75 s, 90 s, 105 s, 120 s, etc.). When the washing time is too short, the waste material can be insufficiently removed leading to contamination in the data sets, slowing data collection, and/or otherwise be detrimental to the sample processing and/or measurement. When the washing time is too long, sample to be measured can be lost (e.g., retention can be low) and/or other problems can arise (e.g., the washing process can damage or change the sample to be measured).

In a specific example of washing the quenched sample, a washing solution can be added to the sample, the sample can be centrifuged, and the supernatant can be aspirated. These steps can be performed concurrently (e.g., contemporaneously, simultaneously, etc.), sequentially, iteratively (e.g., add solution, centrifuge, aspirate, repeat), and/or can be performed in any suitable order and/or manner.

The washed sample (e.g., the constituents to be measured) can be dry, wet (e.g., a wet pellet, include trapped solution, etc.), include solution (e.g., water, buffer, saline, etc.), and/or otherwise be arranged. For example, the washed sample can include about 300 μl (e.g., 50-1000 μl) of buffer solution (e.g., residual buffer solution from the washing solution).

The sample can be washed at ambient temperature (e.g., room temperature, environment temperature, 15-25° C., etc.), at an elevated temperature (e.g., about 25° C., 30° C., 35° C., 40° C., 45° C., etc.), at a depressed temperature (e.g., about 0° C., 10° C., 15° C., etc.), and/or at any suitable temperature.

After quenching and/or washing the sample, the sample is generally stable (e.g., activation state of the sample does not substantially change, the properties of the sample remain approximately the same, etc.). For instance, the sample can be stable on a time scale of minutes to hours (e.g., the sample can be used after these stages, before or after other processes have been performed, for any suitable length of time up to about 24 hours), which can be beneficial for alleviating urgency in performing steps, allow other preparatory steps to be performed, and/or can otherwise be beneficial. However, the sample can additionally or alternatively be unstable (e.g., need to be measured within a threshold amount of time, need to be further processed within a threshold amount of time, etc.) and/or have any suitable stability.

Suspending the washed sample (e.g., the pellet, save sample constituents, etc.) functions to suspend the washed sample in a solution (e.g., buffer solution) to facilitate measurement of the sample. The suspended solution can be referred to as the prepared solution. However, the prepared solution additionally or alternatively include any suitable solutions and/or materials from other processes during the preparation of the sample for measurement and/or any suitable sample. The washed sample is preferably suspended in a buffer solution (e.g., PBS buffer), but can be suspended in water, saline, and/or in any suitable solution.

The washed sample is preferably suspended to a target concentration. The target concentration is preferably between about 4000 and 11000 cells per microliter of solution. However, the target concentration can be less than 4000 cells/μL and/or greater than 11000 cells per μL. The suspended sample preferably has a volume that is approximately 1 mL (e.g., 900 μL to 1.1 mL), but can have a volume less than 1 mL or greater than 1 mL.

The suspended sample is preferably suspended at a target temperature. The target temperature is preferably approximately the same as the measurement temperature, but can be different from the measurement temperature. When the washed sample is at a different temperature than the target temperature, the suspending solution can be heated and/or cooled so that the mixture (e.g., the resulting suspended solution) is at the target temperature. For example, as shown in FIG. 7, the washed sample (e.g., concentrated cells) can be at an ambient temperature (e.g., about 20° C.). The sample temperature can be measured (e.g., using a sensor, using a temperature probe, etc.), inferred (e.g., from ambient temperature, from a temperature of a reagent reservoir, etc.), and/or can otherwise be determined. In this example, the target temperature can be about 25° C. To achieve this target temperature, the buffer solution added to the washed sample can be heated to about 27° C. and added to the washed sample. The temperature of the suspending solution can be empirically determined, heuristically determined, determined based on a thermal mass balance (e.g., accounting for heat capacity, mass, volume, temperature, etc. of the solutions, target suspension, containers, manifolds, etc.), and/or can be determined in any manner. The suspending solution can be heated in the reservoir, in the manifold, in the spindle, in the reagent port, and/or in any suitable location. However, the prepared solution can additionally or alternatively be heated and/or cooled to achieve the target temperature, and/or the prepared sample can be at any suitable temperature (e.g., a temperature where the sample does not degrade).

The suspended solution is preferably transferred to the measurement module. For example, the suspended solution is preferably loaded into the cartridge within the measurement module. The cartridge is preferably at the target temperature (e.g., the measurement temperature such as resulting from S100), but can be at ambient temperature (e.g., to be heated or cooled to the measurement temperature) and/or at any suitable temperature. The suspended solution can be transferred by a user, by a robot, by an automaton, and/or can otherwise be transferred. The amount of sample that is transferred (and ultimately measured) is preferably 0.1-10 mL, but can be less than 0.1 mL and/or greater than 10 mL. For example, about 1 mL (e.g., 1 mL±10%) of suspended sample can be measured. In this example, when more or less sample (e.g., the volume varies by more than a threshold amount) is transferred (e.g., more than 1.1 mL or less than 0.9 mL) the measurement can be suspended, restarted (e.g., with new sample added), and/or the measurement can otherwise be influenced.

After the suspended solution is transferred, the sample preparation system can optionally be washed. For example, a blank solution, buffer solution, water, solvents, and/or any suitable material can be loaded into a sample container, into the washing container and/or any suitable container, which can then be subjected to a washing process similar to the washing performed for the sample. The sample preparation system wash can function to minimize and/or prevent cross-contamination between samples, remove particulate residue, hinder a build-up of particulate residue, and/or can otherwise function.

Measuring the sample S300 preferably functions to acquire data associated with one or more biophysical properties of the sample (and/or patient associated therewith). Measuring the sample is preferably performed using a measurement module, but can be performed using any suitable system and/or component. The data can include: images (e.g., one or more images of each cell), image features, temperature, pressure, flow rate, and/or any suitable data can be acquired. The measured sample is preferably the prepared sample (e.g., suspended sample, washed sample, etc.), but can be the as collected sample, lysed sample, quenched sample, unwashed sample, and/or any suitable sample. In a first specific example, the measured sample can include (e.g., be composed essentially of, consist of, comprise, etc.) leukocytes. In a second specific example, the measured sample can include one or more leukocytes subpopulation (e.g., neutrophils, eosinophils, basophils, monocyte, lymphocytes, etc.) and exclude one or more other leukocyte subpopulations. However, the measured sample can include any suitable cells, species, and/or constituents.

Figure 10:
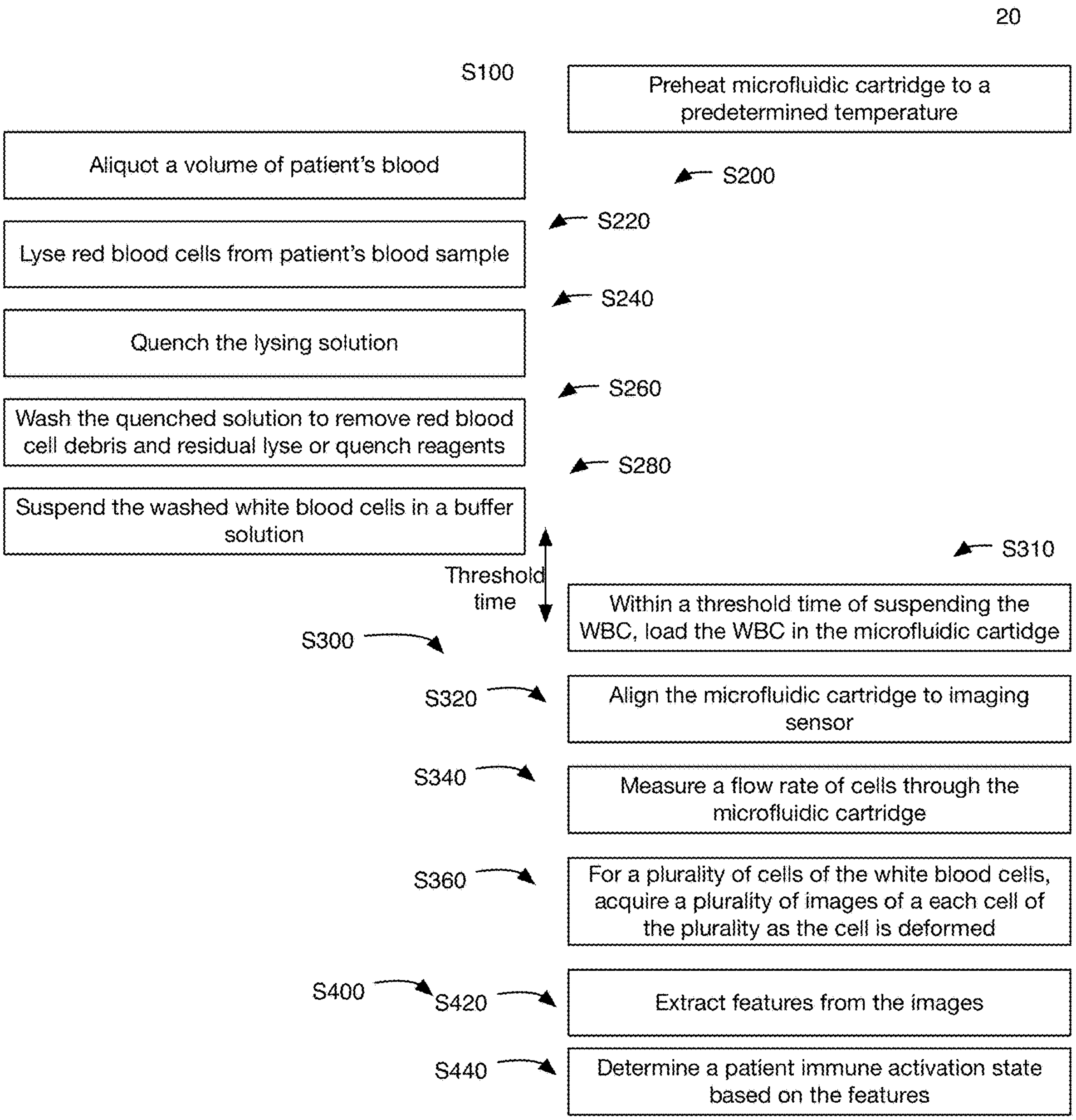
FIG. 10 is a flow chart representation of an example of the method.

The sample is preferably measured within (e.g., the measurement begins within, the measurement is completed by, a portion of the measurement is conducted within, etc.) a threshold amount of time preparing the sample (as shown for example in FIG. 10). The threshold time is preferably on the order of a minute (e.g., 30 seconds, 1 minute, 90 seconds, 2 minutes, 2.5 minutes, 3 minutes, 4 minutes, 5 minutes, values or ranges therebetween, etc.), but can be shorter (e.g., the threshold time can be less than 30 seconds, less than 20 seconds, less than 10 seconds, less than 5 seconds, etc.) and/or longer (e.g., order of tens of minutes, order of an hour, order of a day, etc.). Having the threshold time about a minute (e.g., order of a minute) can be beneficial for limiting the temperature change (e.g., after suspending, heating, etc. the prepared sample), for limiting an amount of sample change (e.g., degradation), and/or can otherwise be beneficial (e.g., whereas larger threshold times may experience, undergo, etc. some of these undesirable effects).

During measuring the sample, the sample temperature is preferably about 25° C. (e.g., 25° C.±1° C., 25° C.±0.5° C., 25° C.±0.3° C., 25° C.±0.1° C., etc.). The measurement temperature can additionally or alternatively be a value between about 15–45° C., less than 15° C., and/or greater than 45° C. Significant deviations (e.g., a deviation from the target temperature that is greater than about 1° C.) from the target measuring temperature can invalidate and/or decrease an accuracy of results from the measurements. Therefore, the sample temperature (and/or the cartridge temperature) is preferably measured throughout the sample measurement. When the sample temperature deviates by more than a threshold amount from the target measurement temperature, the measurement can be paused until the temperature returns to the target measurement temperature, data after the deviation can be excluded from analysis, the method can be ended (e.g., analysis can begin if enough data is present), the method can be restarted (e.g., a new sample can be loaded to be measured, a new sample can be prepared, etc.), a temperature correction can be applied to the data, and/or the method can include any suitable response.

Measuring the sample can include aligning the microfluidic cartridge to the imaging sensor S320. Aligning the microfluidic cartridge can function to set the microfluidic cartridge to the focal plane of the imaging system, to set a predetermined portion (e.g., deformation region, straight region, etc.) of the microfluidic cartridge to the field of view of the imaging system, and/or can otherwise function. The microfluidic cartridge can be aligned using alignment guides (e.g., alignment patterns on the microfluidic cartridge), using a motor (e.g., to translate, rotate, etc. the microfluidic cartridge and/or imaging system), and/or can otherwise be aligned.

Measuring the sample preferably includes acquiring a plurality of images of the measured sample within a flow cytometer (e.g., deformation cytometry) S360. The plurality of images preferably include a plurality of images of cells (or other sample constituents) within a deformation region, extension region, focusing region, straight region, and/or any suitable region of the fluid path (e.g., of the cartridge). However, measuring the sample can additionally or alternatively include performing atomic force microscopy, using a force sensor (e.g., optical force sensor), and/or any suitable data or measurements of the sample can be performed.

The number of measured cells (e.g., per instance of the method, per sample, etc.) is preferably between about 10,000 and 100,000 cells. For example, an average number of cells can be about 55,000 with a standard deviation of about 35,000. In this specific example, approximately 5000 cells/s can be measured. However, the method can measure between about woo cells/s to 10,000 cells/s, less than 1000 cells/s, and/or greater than 10,000 cells/s. When fewer than about 10,000 cells are measured, the method can be restart, can continue until the number of cells exceeds 10,000 (e.g., more cells from the same sample can be added to the measurement), a confidence in the result can be reported (e.g., a flag can be issued based on the number of cells measured), and/or any suitable result can occur. When greater than 100,000 cells are measured, the data can be down sampled (e.g., to select a target number of cells, randomly, based on a probability that a given cell is an outlier, etc.), all measurements can be used, the method can be repeated (e.g., with the same sample, with another sample from the same patient, etc.), the analysis can proceed without change, and/or the analysis or method can be modified in any manner. While fewer cells generally do not provide sufficient data for analysis and additional cells can lead to overfitting and/or slow data analysis, less than 10,000 or greater than 100,000 cells can be measured. However, any suitable number of cells can be measured.

For each measured cell, at least about 10 images (e.g., 10, 11, 12, 14, 15, 16, 17, 20, 25, values or ranges therebetween, >25, etc.) of the cell (within the deformation, extension flow, etc. region of the cytometer) is preferably measured. Having at least 10 images is often sufficient to ensure that event level (e.g., how the cell evolves in response to the forces) analyses can be performed for a cell. When fewer than 10 images of a cell are present, said cell can be excluded from event level analyses, excluded from population analyses, excluded from the set of measured cells (e.g., data rejected), included in frame level analyses, included in event level analyses, can be flagged (e.g., to indicate potential sources for unreliable data), and/or can otherwise be used and/or excluded. However, fewer than 10 images can be used.

Measuring the sample can include determining a flow rate of the sample through the cartridge S340. The flow rate can be determined using a plurality of images, using a flow meter, based on a timing (e.g., how long it takes a metered amount of sample to flow through the cartridge), using a separate flow rate channel (e.g., a separate channel in the microfluidic path), based on an applied pressure or force (e.g., using an equation to calculate the flow rate given the cartridge's dimensions, geometry, etc.), based on thermal changes, using a Coriolis mass flow meter, using acoustics, using electrochemical sensors, and/or in any manner. In an illustrative example, the cartridge can be translated such that a set of flow rate images (e.g., images of one or more cells in a straight region of the cartridge) are acquired; the set of flow rate images can be segmented to identify cells within the flor rate images; based on the frame rate, cell size, cartridge (e.g., fluid channel) size, field of view, and/or any suitable information, calculating the flow rate of the sample through the cartridge. However, the flow rate can be determined in any manner.

The flow rate is preferably determined before measuring the sample (e.g., before acquiring images of cells within the deformation region), but can be determined at any suitable time. By determining (e.g., measuring) the flow rate, the flow rate can be adjusted (if need be) to achieve a target flow rate. The target flow rate is preferably between about 0.1 and 10 m/s (e.g., 0.1 m/s, 0.2 m/s, 0.4 m/s, 1 m/s, 2 m/s, 4 m/s, 10 m/s, values or ranges therebetween, etc.), but can be any suitable flow rate (e.g., less than 0.1 m/s, greater than 10 m/s). The flow rate can depend on the sample concentration, the sample viscosity, an applied force, a frame rate of the imaging sensor, a sample temperature, and/or any suitable property. The flow rate can be adjusted, for instance, by changing a sample concentration, by changing a sample viscosity, by changing an applied pressure (e.g., positive and/or negative pressure or force used to generate the flow), and/or otherwise adjusting the flow rate.

Determining the patient health state S400 preferably functions to determine a health state of the patient. The patient health state is preferably determined using a computing system (e.g., an image analyzer, scoring module, etc. thereof), but can be performed using any suitable component. The patient health state can include an index (e.g., leukocyte structural index, normalized index such as between 0-1, a nonnormalized index such as 0-10, 0-100, 0.1-10, 0.1-100, 1-10, 1-100, etc.), a diagnosis, a classification, a probability of a diagnosis applying to a patient, and/or any suitable information.

The health state can be determined from a model, an equation, a look-up table, a machine learning algorithm (e.g., trained to output a score, trained to output an index, trained to output a disease state, etc.), and/or can otherwise be determined. Examples of models that can be used include: logistic regressions (e.g., linear logistic regressions, nonlinear logistic regressions, etc.), decision trees, Bayesian classifiers, nearest neighbor techniques, support vector machines, decision forests (e.g., random forest), neural networks, gradient boosting, and/or any model can be used. The model can be: a predetermined model, a general model, a model selected based on the auxiliary information, and/or any other suitable model.

Inputs to the model can include: one or more biophysical properties; one or more parameters; auxiliary information such as age, maturity (e.g., infant, toddler, child, adolescent, adult, etc.), weight, height, race, sex, temperature, body mass index, body fat ratio, preexisting conditions, duration of symptoms, onset of symptoms, travel, blood oxygenation levels, blood pressure, infection source, etc.; treatment parameters (e.g., hospital stay; administered treatments; etc.); collection parameters (e.g., temperature; other compounds found in the sample; etc.); images (e.g., from the set of images); images and/or analyses thereof of cells in different illumination conditions (e.g., different intensity light, different wavelength light, etc.); different event level information; frame-level analyses; population analyses; and/or any inputs. In an illustrative example, the inputs can include a trajectory parameter (e.g., an oscillation amplitude, average oscillation amplitude, oscillation amplitude distribution, etc. such as for each cell, for each cell with a threshold value, etc.), a cell size (e.g., thickness), and/or a cell enumeration (e.g., number of neutrophils, number of leukocytes, etc. such as total number of cells, total number of cells with a threshold trajectory parameter, etc.).

Outputs of the model can include: an index (e.g., a health state index; a leukocyte structural index (LSI); a value between 0-1, 0-10, etc.; a score; a number of constituents with a parameter and/or combination of parameters that exceeds a threshold such as the total number of constituents exceeding the threshold, a fraction of the total number of constituents exceeding the threshold, etc.; a probability; etc.), a health state, a health state severity, a probability of a health state, and/or any output.

In an illustrative example, the health state can be determined based on the index. When the index exceeds a threshold (e.g., 0.01, 0.05, 0.1, 0.2, 0.25, 0.3, 0.4, 0.5, 0.6, 0.7, 0.75, 0.8, 0.9, 0.95, 0.99, 1, etc.), the health state can indicate that a patient has (or is likely to have such as probability at least 50%) a condition. When the index is below a threshold (e.g., 0.01, 0.05, 0.1, 0.2, 0.25, 0.3, 0.4, 0.5, 0.6, 0:7, 0.75, 0.8, 0.9, 0.85, 0.99, 1, etc.), the health state can indicate that a patient does not have a condition (or is likely to not such as the probability that the patient does not have the condition is at least 50%). However, the index falling below a threshold can be indicative of a condition, the index exceeding a threshold can be indicative of not having a condition, and/or the index can be used in any manner. The threshold can be determined based on a training dataset (e.g., in a similar manner to how the model is generated, in a similar manner to how the inputs to the model are selected), be predetermined, be determined according to an equation (e.g., an equation based on and/or that accounts for the auxiliary sample information), and/or can be otherwise determined.

In some variants, a single index can be determined (e.g., wherein the population parameters for each cell subpopulation can be aggregated into a single calculation). In other variants, more than one index can be determined for a patient and/or sample. For example, a neutrophil index and a monocyte index can be determined. Each index can have the same threshold or a different threshold. For example, a monocyte index exceeding a threshold of 0.75 can be indicative of a condition and a neutrophil index exceeding a threshold of 0.9 can be indicative of a condition. When a plurality of indices are used, the health state can be determined based on voting, a preferred index, a weighted average of the indices results, an equation relating the indices and/or thresholds, and/or be otherwise determined.

Determining the health state preferably includes determining biophysical properties S430 (e.g., parameters such as structural parameters, trajectory parameters, patient parameters, location parameters, etc.) from the measured data. The biophysical properties are preferably used for the determination of the health state, but can otherwise be used.

The set of biophysical properties preferably correspond to population parameters (e.g., parameters that are representative of the sample), but can correspond to and/or be associated with event parameters (e.g., parameters that are representative of an image such as parameters determined based on a feature or object within the image; parameters that are representative of a constituent such as parameters determined based on a plurality of images of a constituent, a feature, an object, etc.; etc.), frame parameters (e.g., parameters associated with a single image), and/or can correspond to or be associated with any suitable reference. The population parameters can be determined from event parameters, frame parameters, and/or from any suitable parameters and/or can otherwise determined. The population parameters can be an average of a plurality of parameters, a characteristic parameter (e.g., maximum, minimum, mean, median, mode, etc.) of the parameters, and/or can be otherwise related to the parameters. In specific example, determining one or more parameters of the set of parameters can include: averaging the parameters determined for each event (e.g., image, constituent traversal through the device or deformation region, etc.), averaging the parameters that exceed a threshold (e.g., averaging the parameters that are greater than the $10^{th}$, $20^{th}$, $30^{th}$, $40^{th}$, $50^{th}$, $60^{th}$, $70^{th}$, $80^{th}$, $90^{th}$, $95^{th}$, etc. percentile, averaging the parameters that are less than the $5^{th}$, $10^{th}$, $20^{th}$, $30^{th}$, $40^{th}$, $50^{th}$, $60^{th}$, $70^{th}$, $80^{th}$, $90^{th}$, $95^{th}$, etc. percentile, etc.), averaging a subset of the parameters (e.g., parameters associated with the same feature type such as the same cell type), an extrema parameter (e.g., maximum, minimum, etc.), determining a correlation between parameters, determining a variance and/or standard deviation of the set (or a subset) of the event parameters, using an equation relating the event parameters to the population parameters, using a weighted average of the event parameters, determining a regression (e.g., linear regression, nonlinear regression, etc.) between the distribution of event and/or frame parameters, and/or can be otherwise determined.

In an illustrative example, determining a structural parameter can include determining a boundary of the feature (e.g., interior boundary, exterior boundary, etc.) and determining a structural parameter based on the boundary. In a first variation of this illustrative example, the structural parameter can be determined based on the known geometry of the detection system and the sample geometry (e.g., the size of the feature can be determined based on the system geometry and known camera parameters such as focal distance, optical sensor size, etc.). In a second variation of this illustrative example, the structural parameter can be determined by determining a disparity map between two images that include the same feature. In a specific example, the aspect ratio of the cell in each frame and/or position along the deformation region can be determined based on the cell dimensions extracted from the respective frames.

In an illustrative example, determining a trajectory parameter can include: determining a centroid position of the feature (e.g., object, constituent) in each image of the plurality of images, tracking a change in position of the centroid between the plurality of images, measuring an amplitude of an oscillation (e.g., using a one or more peaks or cycles of the oscillation), and calculating a parameter based on the amplitude of the oscillation. In a first variation of this illustrative example, measuring the amplitude can exclude measuring the amplitude of the first, second, and/or any suitable peaks of the oscillation, which can enhance the reproducibility of the measurements. In a second variation of this illustrative example, measuring the amplitude can include measuring the amplitude of the third, fourth, fifth and/or any peaks of the oscillation and averaging the amplitudes to determine the fit parameter. In a third variation of this illustrative example, measuring the amplitude can include measuring the amplitude of the third, fourth, fifth and/or any peaks of the oscillation and fitting the oscillation to a predetermined equation (e.g., an oscillatory function such as trigonometric function, a damped oscillation, an exponential function, etc.) to determine a trajectory parameter (e.g., a fit parameter such as amplitude, offset, phase, frequency, decay, damping, driving, etc.). In a fourth variation of this illustrative example, the trajectory parameter can include one or more Fourier coefficients from a Fourier decomposition (e.g., a Fourier cosine transformation, Fourier sine transformation, Fourier transformation, etc.) of the trajectory. In a fifth variation of this specific example, the trajectory parameter can be determined based on a change in a structural parameter between images that contain the same feature. In a specific example, the VEIR of the cell during flow through the deformation region can be determined based on the cell oscillation amplitude extracted from the respective timeseries of frames. In a sixth variant of this illustrative example, the trajectory parameter can be determined based on the amplitude of a primary, secondary, ternary, quaternary, quintenary (quinary), senary, septenary, octonary, nonary, denary cycle, and/or other cycle of the oscillation, and/or a combination of the above (e.g., excluding some cycles, such as the primary and/or secondary cycles; including a subset of cycles, such as only the ternary, quaternary, and quintenary cycles; etc.). However, the trajectory parameter can be otherwise determined.

Determining the biophysical properties can include detecting overlapping cells within the images. When overlapping cells are detected, the cells can be excluded from the analysis (e.g., frames where the cells overlap can be excluded, events including one or more overlapping cells can be excluded, etc.), the cells can be separated (e.g., using a machine learning algorithm), a correction can be applied based on the overlap (e.g., extent of overlap), and/or the overlapping cells can otherwise be handled.

Figure 11:
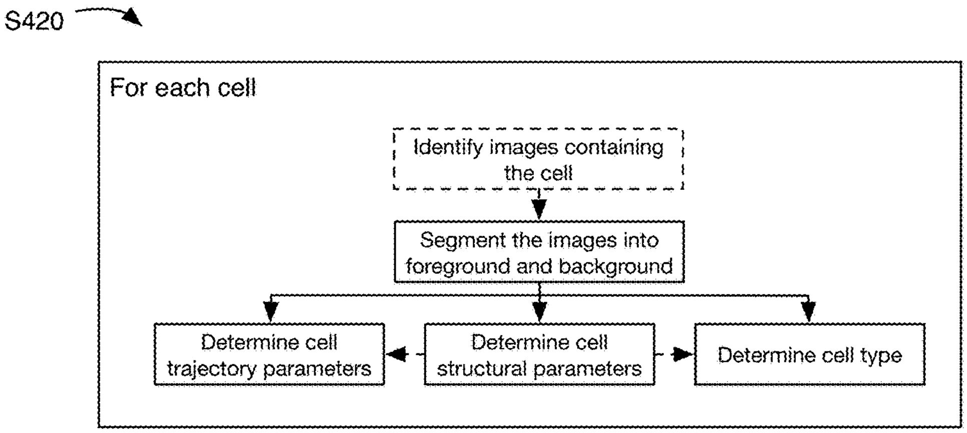
FIG. 11 is a flow chart representation of an example of an analysis performed for a cell of the white blood cells.

In a specific example (as shown for example in FIG. 11 and/or FIG. 12), determining the patient health state can include: receiving images of cells (e.g., leukocytes) during deformation; for each cell, extracting cell features from the images S420 (e.g., dimensions and position within the flow region); for each cell, determining a trajectory parameter (e.g., oscillation amplitude) and/or a structural parameter (e.g., aspect ratio) based on the cell features; calculating an index based on the trajectory parameter and/or structural parameter values S435; and determining a health condition of the patient based on the index S440. The method can optionally include separating the cell data according to cell subpopulation (e.g., monocyte, lymphocyte, neutrophil), wherein the index can be calculated based on the parameters for a subset of the cell subpopulations (e.g., monocytes and neutrophils).

In a second specific example, determining the patient health state can be performed as disclosed in U.S. patent application No. 17/401,627, titled "SYSTEM AND METHOD FOR IMMUNE ACTIVITY DETERMINATION" filed on 13 Aug. 2021, and incorporated in its entirety by this reference.

However, the patient health state can otherwise be determined.

Provisioning an intervention S500 can function to provide an intervention to the patient. The intervention preferably depends on the health state (e.g., immune activation state), but can depend on the biophysical properties, patient data, and/or any suitable data and/or information. Provisioning an intervention is preferably performed automatically (e.g., a computing system generates a suggestion based on the health state), but can be performed manually and/or in any manner. Examples of interventions include: tracking the patient's disease state progression over time, determining a treatment parameter (e.g., estimated hospital stay duration, estimated triage requirements, etc.), initiating secondary analyses (e.g., innate immune activation assays such as light microscopy to assay structural features; cytology assays; chemical change assays such as using immunofluorescence labeling of CD11b, CD18, CD64, CD66b, flow cytometry, etc.; transcriptomic signatures analyses; etc.), suggesting an antibiotic regiment, suggesting an antiviral regiment, suggesting a chemotherapy regiment, informing a health care provider of a patient health state, indicating an urgency of a health state, informing a patient of a health state, displaying a health state, and/or other suitable interventions.

The methods of the preferred embodiment and variations thereof can be embodied and/or implemented at least in part as a machine configured to receive a computer-readable medium storing computer-readable instructions. The computer-readable medium can be stored on any suitable computer-readable media such as RAMs, ROMs, flash memory, EEPROMs, optical devices (CD or DVD), hard drives, floppy drives, or any suitable device. The computer-executable component is preferably a general or application specific processor, but any suitable dedicated hardware or hardware/firmware combination device can alternatively or additionally execute the instructions.

Embodiments of the system and/or method can include every combination and permutation of the various system components and the various method processes, wherein one or more instances of the method and/or processes described herein can be performed asynchronously (e.g., sequentially), concurrently (e.g., in parallel), or in any other suitable order by and/or using one or more instances of the systems, elements, and/or entities described herein.

As a person skilled in the art will recognize from the previous detailed description and from the figures and claims, modifications and changes can be made to the preferred embodiments of the invention without departing from the scope of this invention defined in the following claims.

We claim:

1. A system for diagnosing a probability of sepsis in a patient comprising:
- a sample preparation subsystem comprising:
  - a sample holder configured to retain a test tube comprising a blood sample from the patient;
  - a spindle configured to attach to the test tube via a seal, wherein the spindle comprises one or more reagent ports fluidly connected to a reagent reservoir, and to a vacuum pump, wherein the spindle is configured to centrifuge the blood sample within the test tube to generate a prepared blood sample;
- a cytometry module comprising:
  - a microfluidic cartridge configured to receive the prepared blood sample from the sample preparation subsystem, wherein the microfluidic cartridge comprises a microfluidic channel with a deformation region wherein a stress is applied to cells within the deformation region;
  - a heating element configured to maintain a temperature of the microfluidic cartridge at a target temperature;
  - an imaging system comprising an image sensor and a microscope; and
  - a pressure system connected to the microfluidic channel, wherein the pressure system displaces the prepared blood sample through the microfluidic cartridge; and
- an image analysis system configured to:
  - analyze images of the prepared blood sample acquired using the imaging system; and
  - determine the probability that the patient has sepsis.

2. The system of claim 1, wherein the sample holder is connected to a stepper motor, wherein reagents are added to the blood sample depending on a position of the sample holder.

3. The system of claim 1, wherein the reagent reservoir comprises at least one of a lysis solution, a quench solution, or a buffer solution.

4. The system of claim 3, wherein the lysis solution comprises formic acid, the quench solution comprises a basic solution, and the buffer solution comprises phosphate-buffered saline (PBS).

5. The system of claim 1, wherein a temperature of the prepared blood sample is 25° C.±1° C.

6. The system of claim 1, wherein a target temperature of the prepared blood sample is 25° C.±0.5° C.

7. The system of claim 1, wherein the probability that the patient has sepsis is determined within about 10 minutes of introducing the blood sample in the sample holder.

8. The system of claim 1, wherein a flow of the prepared blood sample within the cytometry module is established using compressed air with a pressure of 90±10 PSI.

9. The system of claim 1, wherein a flow of the prepared blood sample within the cytometry module is established using compressed air with a pressure of 91±3 PSI.

10. The system of claim 1, wherein the prepared blood sample comprises a suspended sample.

11. The system of claim 10, wherein the suspended sample comprises one or more leukocyte populations.

12. The system of claim 1, wherein the microfluidic cartridge further comprises an inlet, a focusing region fluidically connected to the inlet, and an outlet.

13. The system of claim 1, wherein a frame rate of the image sensor of the imaging system is at least 1,000 frames per second.

14. The system of claim 1, wherein the imaging system is further configured to acquire images of the cells in a channel upstream of the deformation region.

15. The system of claim 1, wherein the image analysis system is configured to determine the probability of sepsis in the patient based on one or more biophysical properties of the cells.

16. The system of claim 15, wherein the one or more biophysical properties of the cells comprise at least one of a trajectory parameter, a cell count, or a leukocyte subpopulation.

17. The system of claim 16, wherein the trajectory parameter comprises an oscillation of a centroid of a cell of the cells.

18. The system of claim 1, wherein the blood sample is centrifuged with a relative centrifugal force of about 500 g to about 5000 g.

19. The system of claim 1, wherein the centrifugation of the blood sample separates one or more species of the sample based on solubility, density, or mass.

20. The system of claim 19, wherein the separation of the blood sample comprises separation of white blood cells and red blood cells.

* * * * *